US008530654B2

(12) United States Patent
Yamamoto et al.

(10) Patent No.: US 8,530,654 B2
(45) Date of Patent: *Sep. 10, 2013

(54) CRYSTALS, AMORPHOUS SUBSTANCES OR SALTS OF METHYL N-[3-(6,7-DIMETHOXY-2-METHYLAMINOQUINAZOLIN-4-YL) PHENYL] TEREPHTHALAMIC ACID

(75) Inventors: Eiichi Yamamoto, Tsukuba (JP); Osamu Asano, Tsukuba (JP); Jun Niijima, Tsukuba (JP); Kazumasa Nara, Tsukuba (JP)

(73) Assignee: Eisai R&D Management Co., Ltd., Tokyo (JP)

( * ) Notice: Subject to any disclaimer, the term of this patent is extended or adjusted under 35 U.S.C. 154(b) by 1324 days.

This patent is subject to a terminal disclaimer.

(21) Appl. No.: 12/032,550

(22) Filed: Feb. 15, 2008

(65) Prior Publication Data

US 2009/0062539 A1 Mar. 5, 2009

Related U.S. Application Data

(63) Continuation-in-part of application No. 11/707,904, filed on Feb. 20, 2007, now Pat. No. 7,939,540.

(60) Provisional application No. 60/956,598, filed on Aug. 17, 2007.

(30) Foreign Application Priority Data

| Feb. 16, 2007 | (TW) | ................................ 96105966 A |
| Feb. 19, 2007 | (PK) | ...................................... 165/2007 |
| Feb. 19, 2007 | (TH) | ................................ 0701000756 |
| Feb. 20, 2007 | (WO) | .................. PCT/JP2007/053066 |
| Aug. 17, 2007 | (JP) | ................................ P2007-212910 |

(51) Int. Cl.
*C07D 239/84* (2006.01)
*A61K 31/517* (2006.01)

(52) U.S. Cl.
USPC ...................................... 544/293; 514/266.4

(58) Field of Classification Search
USPC ........................................................ 544/293
See application file for complete search history.

(56) References Cited

U.S. PATENT DOCUMENTS

| 5,385,907 | A | 1/1995 | Asakura et al. |
| 6,352,989 | B1 | 3/2002 | Miyazaki et al. |
| 6,740,662 | B1 | 5/2004 | Iwata et al. |
| 6,800,644 | B2 | 10/2004 | Miyazaki et al. |
| 2006/0258703 | A1 | 11/2006 | Shii et al. |
| 2007/0299094 | A1 | 12/2007 | Miyazaki et al. |

FOREIGN PATENT DOCUMENTS

| CA | 2 306 985 A1 | 4/1999 |
| CA | 2 637 573 A1 | 8/2007 |
| EP | 1 992 622 B1 | 7/2011 |
| EP | 2 202 229 B1 | 3/2012 |
| JP | 5-17481 A | 1/1993 |
| JP | 8-165251 A | 6/1996 |
| JP | 11-209350 A | 8/1999 |
| JP | 2001-192385 A | 7/2001 |
| JP | 2001-520196 A | 10/2001 |
| JP | 2005-29541 A | 2/2005 |
| JP | 2005-47909 A | 2/2005 |
| JP | 2005-529930 A | 10/2005 |
| JP | 2005-537262 A | 12/2005 |
| JP | 4778550 B2 | 9/2011 |
| WO | WO 98/10767 A2 | 3/1998 |
| WO | WO 99/20280 A1 | 4/1999 |
| WO | WO-99/37622 A1 | 7/1999 |
| WO | WO 03/099278 A1 | 12/2003 |
| WO | WO 2004/006920 A1 | 1/2004 |
| WO | WO 2005/082865 A1 | 9/2005 |
| WO | WO-2006/093226 A1 | 9/2006 |
| WO | WO 2006/093226 A1 | 9/2006 |
| WO | WO 2007/097317 A1 | 8/2007 |
| WO | WO-2008/099887 A1 | 8/2008 |

OTHER PUBLICATIONS

Extended European Search Report mailed Aug. 11, 2010 in Application No. 08827867.6.
English translations of the Notification of Transmittal of the International Preliminary Report on Patentability (Form PCT/IB/338), International Preliminary Report on Patentability (Form PCT/IB/373), and Written Opinion of the International Searching Authority(Form PCT/ISA/237) issued Aug. 27, 2009 for PCT/JP2008/052448.
International Preliminary Report on Patentability (Forms PCT/IB338 and PCT/IB/373) snd Written Opinion of the International Searching Authority (Form PCT/ISA/237), mailed Mar. 18, 2010, for International Application No. PCT/JP2008/064621.
U.S. Office Action, dated Oct. 5, 2010, for copending U.S. Appl. No. 11/707,904.
Yakuji Nippo Limited, "Iyakuhin Tenkabutsu Jiten 2007" ("Pharmaceutical Excipients Dictionary 2007"), Edited by Japan Pharmaceutical Excipients Council, Jul. 25, 2007, pp. 279-280.
Yakuji Nippo Limited, "Iyakuhin Tenkabutsu Jiten 2007" ("Pharmaceutical Excipients Dictionary 2007"), Edited by Japan Pharmaceutical Excipients Council, Jul. 25, 2007, pp. 280-282 and 309.
English translations of the Notification of Transmittal of the international Preliminary Report on Patentability (Form PCT/IB/338), International Preliminary Report on Patentability (Form PCT/IB/373), Written Opinion of the International Searching Authority (Form PCT/ISA/237) issued Mar. 18, 2010 and International Search Report (Form PCT/ISA/210) issued Sep. 9, 2008 for International Application No. PCT/JP2008/064620.
Greene et al., "Protective Groups in Organic Synthesis," Third Edition, Protection for the Amino Group, 1999, pp. 518-525, pp. 551-555.

(Continued)

*Primary Examiner* — Susanna Moore
(74) *Attorney, Agent, or Firm* — Birch, Stewart, Kolasch & Birch, LLP

(57) ABSTRACT

Crystals, amorphous substances, salts, and hydrates of a salt of methyl N-[3-(6,7-dimethoxy-2-methylaminoquinazolin-4-yl)phenyl]terephthalamic acid having PDE4 inhibitory action are provided. These compounds are useful for treating allergic diseases such as atopic dermatitis.

1 Claim, 16 Drawing Sheets

(56) References Cited

OTHER PUBLICATIONS

Hanifin et al., Journal of Investigative Dermatology, vol. 107, No. 1, Jul. 1996, pp. 51-56.
International Search Report mailed Sep. 9, 2008 in International Application No. PCT/JP2008/064621.
Klein et al., Archives of Dermatology, vol. 135, Dec. 1999, pp. 1522-1525.
Leung et al., The Lancet, vol. 361, No. 9352, Jan. 11, 2003, pp. 151-160.
Schmidt, MD et al., "The phosphodiesterase 4 inhibitor roflumilast is effective in the treatment of allergic rhinitis," Journal of Allergy and Clinical Immunology, vol. 108, No. 4, 2001, pp. 530-536.
Yosipovitch et al., The Lancet, vol. 361, No. 9358, Feb. 22, 2003, pp. 690-694.
"The Fourth Series of Experimental Chemistry", vol. 1, Fundamental Procedure I, Edited by the Chemical Society of Japan, Maruzen Co., Ltd., p. 184-186, (1990).
Response filed Feb. 8, 2012, in reply to the Official Communication Pursuant to Art. 94(3) EPC daetd Nov. 11, 2011, issued in European Patent Application No. 08 177 290.0.
Office Action dated Feb. 13, 2012, issued in Australian Patent Application No. 2008290000.
Notification of Second Office Action issed Feb. 15, 2012, in Chinese Patent Application No. 200880005202.8, with English translation.
Office Action dated Mar. 8, 2012, issued in Norwegian Patent Application No. 20083980, with English translation.
Examiner's First Report issued Feb. 14, 2012, in Australian Patent Application No. 2008290001.
Office Action issued Dec. 20, 2012, in Taiwan Patent Application No. 097131272, with English translation.
Office Action issued Jan. 3, 2013, in Taiwan Patent Application No. 096105966, with English translation.
Notification to Complete Registration Formalities issued Jan. 17, 2013, in Chinese Patent Application No. 200680022003.8, with English translation.
Notice of Allowance issued Feb. 19, 2913. In U.S. Appl. No. 12/733,169.
Notice of Deficiencies in Israeli Patent Application No. 193322, dated Oct. 28, 2012.
Office Action issued Apr. 19, 2013, in Canadian Patent Application No. 2,6,78,477.
Amendment filed Oct. 26, 2009, Australian Patent Application No. 2008215411.
Amendment filed Sep. 17, 2009, in Korean Patent Application No. 10-2009-7007623, with English translation.
Amendment recieved before Examination, filed Aug. 6, 2009, in European Patent Application No. 08711290.0.
Communication Pursuant to Article 94(3) issued Nov. 11, 2011, in European Patent Application No. 08711290.0.
Communication Pursuant to Rules 70(2) and 70a(2) EPC (Invitation to Declare Maintenance) issued Jun. 7, 2011, in European Patent Application No. 08711290.0.
Extended European Search Report issued May 20, 2011, in European Patent Application No. 08711290.0.
Notice Priot to Examination issued Jun. 17, 2010, in Israel Patent Application No. 199760, with English translation.
Office Action issued Aug. 23, 2011, in Chinese Patent Application No. 200880005202.8, with English translation.
Feb. 8, 2012, in response to Communication Pursuant to Article 94(3) issued Nov. 11, 2011, in European Patent Application No. 08711290. 0.
Nov. 18, 2011, in Chinese Patent Application No. 20088005202.8, with English translation.
Response to Invitation to Declare Maintenace and Reply to Search Report filed Jul. 12, 2011, in European Patent Application No. 08711290.0.
Voluntary Amendment filed Aug. 14, 2009, in Chinese Patent Application No. 200880005202.8, with English translation.
Voluntary Amendment filed Aug. 17, 2009, in Canadian Patent Application No. 2678477.
Amendment as filed Apr. 20, 2012, in Chinese Patent Application No. 200880005202.8, with English translation.
Response filed Apr. 20, 2012, in Chinese Patent Application No. 200880005202.8, with English translation.
Notice of Acceptance issued May 1, 2012, in Australian Patent Application No. 2008290000.
Notice of Allowance dated May 4, 2012, issued in Chinese Patent Application No. 200880022081.8, with English translation.
Office Action issued Mar. 21. 2013, in Canadian Patent Application No, 2,696,727.
Notice of Reasons for Rejection issued May 15, 2012 in Japanese Patent Application No. P2009-529019, with English translation.
Official Action dated May 7, 2012, in Norwegian Patent Application No. 20083980, with English translation.
Notification to Complete Registration Formalities issued Jun. 6, 2012, in Chinese Patent Application No. 200880005202.8, with English translation.
Notification to Grant Patent Right for Invention dated Jun. 6, 2012, issued in Chinese Patent Application No. 200880005202.8, with English translation.
Decision of Patent Grant issued Jul. 10, 2012, in Japanese Patent Application No. P2009-529018, with English translation.
Notice of Acceptance issued Jul. 26, 2012, in Australian Patent Application No. 2008290001.
Request for Suspension After Filing a Response to the Notice Prior to Examination filed Sep. 23, 2012, in Israeli Patent Application No. 199760, with English translation.
Notie of Reason for Rejection issued Jun. 26, 2012, in Japanese Patent Application No. P2008-558123, with English translation.
Office Action issued Jun. 13, 2012, in U.S. Appl. No. 12/673,715.
Final Decision issued Sep. 25, 2012, in Japanese Patent Application No. P2008-558123.
Examination Response filed Oct. 4, 2012, in reply to the first Examination Report issued May 31, 2012, in Australian Patent Application No. 2008215411.
Notice Prior to Allowance issued Sep. 19, 2012, in Israeli Patent Application No. 204017, with English translation.
Examiner's First Response issued May 31, 2012, in Australian Patent Application No. 2008215411.
Office Action issued Aug. 1, 2012, in U.S. Appl. No. 12/733,169.
Chinese Office Action issued on Jul. 4, 2012 in Chinese Application No. 2008-80022003.8, with English translation.
Decision of Patent Grant issued Jul. 20, 2012 in Japanese Application No. P2009-529019, with English translation.
Notice of Reason for Rejection issued Jul. 24, 2012 in Japanese Application No. P2008-558123, with English translation.
Notice of Deficiencies in Patent Application issued Oct. 28. 2012, in Israel Patent Application No. 204018, with English translation.
Notice of Allowance issued Nov. 14, 2012, in Norweigan Patent Application No. 20083980, with English translation.
Notice of Allowance issued Nov. 23. 2012, in Canadian Patent Application No. 2,637,573.
Office Action issued Nov. 20, 2012, in Korean Patent Application No. 10-2008-7021869, with English translation.
Amendment After Allowance filed Jan. 9, 2013, in Canadian Patent Application No. 2,637,573.
Notice of Allowance issued Jan. 9, 2013, in U.S. Appl. No. 12/673,715.
Notice of Acceptance issued Nov. 12, 2012, in Australian Patent Application No. 2008215411.
Notice of Allowance Issued Apr. 16, 2013, in U.S. Appl. No. 12/673,715.
Written Decision of Allowance from Intellectual Property Office issued May 7, 2013, in Taiwanese Patent Application No. 096105968, with English translation.
Notice of Allowance issued May 20, 2013, in Korean Patent Application No. 10-2008-7021859, with English translation.
Communication Pursuant to Article 94(3) EPC issued Jul. 23, 2013, in European Patent Application No. 08711290.0.

CRYSTALS, AMORPHOUS SUBSTANCES OR SALTS OF METHYL N-[3-(6,7-DIMETHOXY-2-METHYLAMINOQUINAZOLIN-4-YL)PHENYL] TEREPHTHALAMIC ACID

RELATED APPLICATIONS

This is a continuation-in-part application of U.S. patent application Ser. No. 11/707,904 filed on Feb. 20, 2007 now U.S. Pat. No. 7,939,540. And, this application claims priority to U.S. provisional application 60/956,598 filed on Aug. 17, 2007, Japanese patent application 2007-212,910 filed on Aug. 17, 2007, Pakistan patent application 165/2007 filed on Feb. 19, 2007, Thai patent application 0701000756 filed on Feb. 19, 2007, Taiwan patent application 096105966 filed on Feb. 16, 2007, and international patent application PCT/JP2007/053066 filed on Feb. 20, 2007, all of which are herein incorporated by reference in their entirety.

BACKGROUND OF THE INVENTION

1. Field of the Invention

The present invention relates to crystals, amorphous substances, salts, and hydrates of salt of methyl N-[3-(6,7-dimethoxy-2-methylaminoquinazolin-4-yl)phenyl]terephthalamic acid.

2. Related Background Art

Compounds having an inhibitory action against phosphodiesterase 4 (PDE4) have been expected to be useful for treating allergic diseases such as atopic dermatitis. For example, Patent Document 1 discloses a compound having the following structural formula as a compound having a PDE4 inhibitory action.

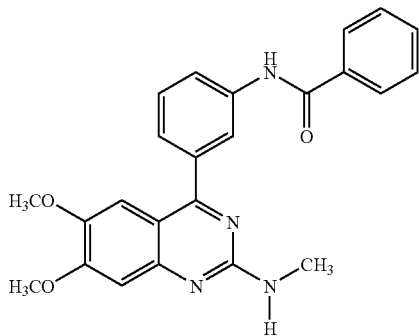 [SMILES: CNc1nc(-c2cccc(NC(=O)c3ccccc3)c2)c2cc(OC)c(OC)cc2n1]

Further, Patent Document 2 describes that the compound having a PDE4 inhibitory action described in Patent Document 1 is useful for treating allergic diseases.
[Patent Document 1] WO 99/37622
[Patent Document 2] WO 06/093226

SUMMARY OF THE INVENTION

The present inventors have found methyl N-[3-(6,7-dimethoxy-2-methylaminoquinazolin-4-yl)phenyl]terephthalamic acid, etc. to be superior PDE4 inhibitors compared to the compound described in Patent Document 1. An object of the present invention is to provide crystals, amorphous substances and salts of methyl N-[3-(6,7-dimethoxy-2-methylaminoquinazolin-4-yl)phenyl]terephthalamic acid.

After tremendous research efforts, the present inventors have reached the present invention.

Specifically, the present invention provides the following <1> to <13>.

<1> Crystals of methyl N-[3-(6,7-dimethoxy-2-methylaminoquinazolin-4-yl)phenyl]terephthalamic acid or hydrate thereof.

<2> Crystals of methyl N-[3-(6,7-dimethoxy-2-methylaminoquinazolin-4-yl)phenyl]terephthalamic acid, which have diffraction peaks at diffraction angles (2θ±0.2°) of 8.2°, 16.5° and/or 24.5° in an X-ray powder diffraction.

<3> Crystals of methyl N-[3-(6,7-dimethoxy-2-methylaminoquinazolin-4-yl)phenyl]terephthalamic acid, which have diffraction peaks at diffraction angles (2θ±0.2°) of 9.4°, 16.8° and/or 23.3° in an X-ray powder diffraction.

<4> Crystals of methyl N-[3-(6,7-dimethoxy-2-methylaminoquinazolin-4-yl)phenyl]terephthalamic acid hydrate, which have diffraction peaks at diffraction angles (2θ±0.2°) of 8.6°, 9.1° and/or 23.2° in an X-ray powder diffraction.

<5> Crystals of methyl N-[3-(6,7-dimethoxy-2-methylaminoquinazolin-4-yl)phenyl]terephthalamic acid hydrate, which have diffraction peaks at diffraction angles (2θ±0.2°) of 7.0°, 10.4° and/or 12.6° in an X-ray powder diffraction.

<6> Crystals of methyl N-[3-(6,7-dimethoxy-2-methylaminoquinazolin-4-yl)phenyl]terephthalamic acid hydrate, which have diffraction peaks at diffraction angles (2θ±0.2°) of 5.4°, 10.9° and/or 11.9° in an X-ray powder diffraction.

<7> An amorphous substance of methyl N-[3-(6,7-dimethoxy-2-methylaminoquinazolin-4-yl)phenyl]terephthalamic acid.

<8> A salt of methyl N-[3-(6,7-dimethoxy-2-methylaminoquinazolin-4-yl)phenyl]terephthalamic acid or hydrate thereof.

<9> An inorganic acid salt of methyl N-[3-(6,7-dimethoxy-2-methylaminoquinazolin-4-yl)phenyl]terephthalamic acid or hydrate thereof.

<10> An organic acid salt of methyl N-[3-(6,7-dimethoxy-2-methylaminoquinazolin-4-yl)phenyl]terephthalamic acid or hydrate thereof.

<11> The inorganic acid salt of methyl N-[3-(6,7-dimethoxy-2-methylaminoquinazolin-4-yl)phenyl]terephthalamic acid or a hydrate thereof according to <9>, wherein the inorganic acid salt is hydrochloride, hydrobromide, sulfate or phosphate.

<12> The organic acid salt of methyl N-[3-(6,7-dimethoxy-2-methylaminoquinazolin-4-yl)phenyl]terephthalamic acid or hydrate thereof according to <10>, wherein the organic acid salt is methanesulfonate or p-toluenesulfonate.

<13> Crystals of methyl N-[3-(6,7-dimethoxy-2-methylaminoquinazolin-4-yl)phenyl]terephthalamic acid, which have peaks at chemical shifts of approximately 146.19 ppm, approximately 102.78 ppm and/or approximately 27.47 ppm in a $^{13}C$ solid NMR spectrum.

The crystals, amorphous substances, salts and salt hydrates of methyl N-[3-(6,7-dimethoxy-2-methylaminoquinazolin-4-yl)phenyl]terephthalamic acid according to the present invention have an inhibitory action on PDE4 and are useful for treating allergic diseases such as atopic dermatitis.

DESCRIPTION OF THE PREFERRED EMBODIMENTS

Figure 1:
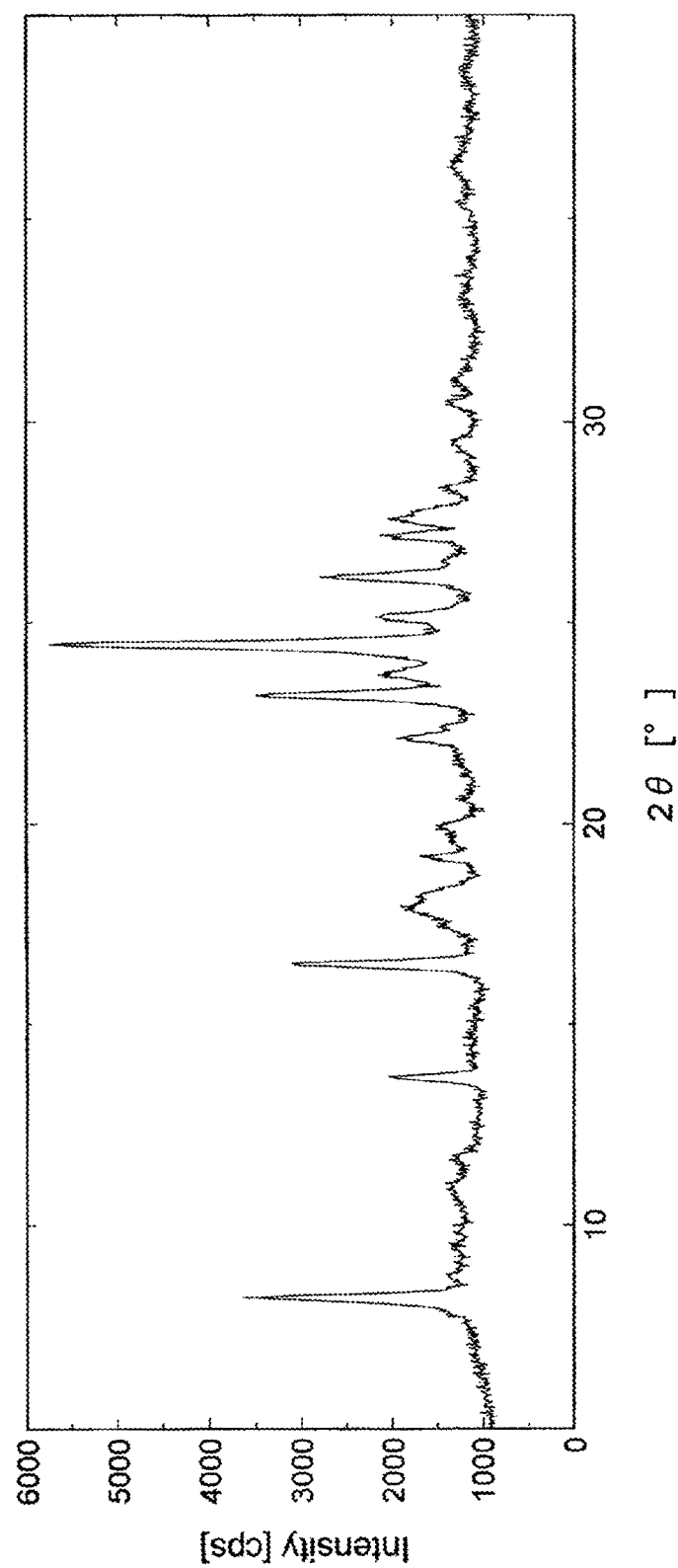
FIG. 1 shows an X-ray powder diffraction pattern for the crystals obtained in Example 2.

In the following the details of the present invention will be described.

The first crystals of methyl N-[3-(6,7-dimethoxy-2-methylaminoquinazolin-4-yl)phenyl]terephthalamic acid have diffraction peaks at diffraction angles (2θ±0.2°) of 8.2°, 16.5° and/or 24.5° in an X-ray powder diffraction. The crystals have peaks at chemical shifts of approximately 146.19 ppm, approximately 102.78 ppm and/or approximately 27.47 ppm in a $^{13}C$ solid NMR spectrometry.

The second crystals of methyl N-[3-(6,7-dimethoxy-2-methylaminoquinazolin-4-yl)phenyl]terephthalamic acid have diffraction peaks at diffraction angles (2θ±0.2°) of 9.4°, 16.8° and/or 23.3° in an X-ray powder diffraction.

The first crystals of methyl N-[3-(6,7-dimethoxy-2-methylaminoquinazolin-4-yl)phenyl]terephthalamic acid hydrate have diffraction peaks at diffraction angles (2θ±0.2°) of 8.6°, 9.1° and/or 23.2° in an X-ray powder diffraction.

The second crystals of methyl N-[3-(6,7-dimethoxy-2-methylaminoquinazolin-4-yl)phenyl]terephthalamic acid hydrate have diffraction peaks at diffraction angles (2θ±0.2°) of 7.0°, 10.4° and/or 12.6° in an X-ray powder diffraction.

The third crystal of methyl N-[3-(6,7-dimethoxy-2-methylaminoquinazolin-4-yl)phenyl]terephthalamic acid hydrate have diffraction peaks at diffraction angles (2θ±0.2°) of 5.4°, 10.9° and/or 11.9° in an X-ray powder diffraction.

Generally, a diffraction angle (2θ) in an X-ray powder diffraction can have an error within the range of ±0.2°, and therefore, it should be understood that the values of the above described diffraction angles also include those with an error within the range of about ±0.2°. Accordingly the present invention includes not only crystals whose diffraction angles in an X-ray powder diffraction completely correspond to the above described values, but also crystals whose diffraction angles correspond to the above described values with an error within the range of ±0.2°.

Further, the expression "having diffraction peaks at diffraction angles (2θ±0.2°) of α°, β° and/or γ°" means having at least one of the above diffraction peaks.

Generally, a chemical shift (ppm) in a $^{13}C$ solid NMR spectrum can have a certain degree of error, and therefore, it is understood that the present invention includes not only crystals whose peaks (chemical shifts) in the respective $^{13}C$ solid NMR spectra completely correspond to the above values, but also crystals whose peaks are observed at substantially the same chemical shifts when $^{13}C$ solid NMR spectrum measurements are made under ordinal measuring conditions or under the substantially same conditions as those described herein, more specifically crystals whose peaks are observed at the above described values with an error within the range of about ±0.5 ppm. In other words, the present invention includes not only crystals whose peaks (chemical shifts) completely correspond to the above described values, but also crystals whose peaks (chemical shifts) correspond to the above described values with an error of about ±0.5 ppm.

Further, the expression "having peaks at chemical shifts of approximately α ppm, approximately β ppm and/or approximately γ ppm" means having at least one of the peaks at the above described chemical shifts.

Methyl N-[3-(6,7-dimethoxy-2-methylaminoquinazolin-4-yl)phenyl]terephthalamic acid can be produced by, for example, the method described in Example 1 below.

The first crystals of methyl N-[3-(6,7-dimethoxy-2-methylaminoquinazolin-4-yl)phenyl]terephthalamic acid can be produced by dissolving methyl N-[3-(6,7-dimethoxy-2-methylaminoquinazolin-4-yl)phenyl]terephthalamic acid in acetonitrile and precipitating crystals from the solution. More particularly, the first crystals of methyl N-[3-(6,7-dimethoxy-2-methylaminoquinazolin-4-yl)phenyl]terephthalamic acid can be produced by dissolving methyl N-[3-(6,7-dimethoxy-2-methylaminoquinazolin-4-yl)phenyl]terephthalamic acid in acetonitrile at room temperature or under heating and slowly cooling the solution to 4° C. to room temperature to precipitate crystals from the solution.

The amount of acetonitrile used can be appropriately selected, provided that the lower limit is the amount that enables the dissolution of methyl N-[3-(6,7-dimethoxy-2-methylaminoquinazolin-4-yl)phenyl]terephthalamic acid by heating and the upper limit is the amount that does not decrease the yield of the crystals significantly.

The heating temperature can be appropriately selected from the temperatures which enable methyl N-[3-(6,7-dimethoxy-2-methylaminoquinazolin-4-yl)phenyl]terephthalamic acid to be dissolved in acetonitrile, but preferably the heating temperature is 50° C. to the reflux temperature of the solvent for recrystallization. The rate of slow cooling can be 5 to 30° C./hour. More particularly, the first crystals of methyl N-[3-(6,7-dimethoxy-2-methylaminoquinazolin-4-yl)phenyl]terephthalamic acid can be produced by the method described in Example 2 below. The first crystals of methyl N-[3-(6,7-dimethoxy-2-methylaminoquinazolin-4-yl)phenyl]terephthalamic acid can also be produced by the method described in Example 8 below.

The second crystals of methyl N-[3-(6,7-dimethoxy-2-methylaminoquinazolin-4-yl)phenyl]terephthalamic acid can be produced by dissolving methyl N-[3-(6,7-dimethoxy-2-methylaminoquinazolin-4-yl)phenyl]terephthalamic acid in 2-propanol and precipitating crystals from the solution. More particularly, the second crystals of methyl N-[3-(6,7-dimethoxy-2-methylaminoquinazolin-4-yl)phenyl]terephthalamic acid can be produced by dissolving methyl N-[3-(6,7-dimethoxy-2-methylaminoquinazolin-4-yl)phenyl] terephthalamic acid in 2-propanol at room temperature or under heating and slowly cooling the solution to 4° C. to room temperature to precipitate crystals from the solution.

The amount of 2-propanol used can be appropriately selected, provided that the lower limit is the amount that enables the dissolution of methyl N-[3-(6,7-dimethoxy-2-methylaminoquinazolin-4-yl)phenyl]terephthalamic acid by heating and the upper limit is the amount that does not decrease the yield of the crystals significantly. The heating temperature can be appropriately selected from the temperatures which enable methyl N-[3-(6,7-dimethoxy-2-methylaminoquinazolin-4-yl)phenyl]terephthalamic acid to be dissolved in 2-propanol, but preferably the heating temperature is 50° C. to the reflux temperature of the solvent for recrystallization. The rate of slow cooling can be 5 to 30° C./hour.

More particularly, the second crystals of methyl N-[3-(6,7-dimethoxy-2-methylaminoquinazolin-4-yl)phenyl]terephthalamic acid can be produced by the method described in Example 3 below.

The first crystals of methyl N-[3-(6,7-dimethoxy-2-methylaminoquinazolin-4-yl)phenyl]terephthalamic acid hydrate can be produced by dissolving methyl N-[3-(6,7-dimethoxy-2-methylaminoquinazolin-4-yl)phenyl]terephthalamic acid in acetone and precipitating crystals from the solution. More particularly, the first crystals of methyl N-[3-(6,7-dimethoxy-2-methylaminoquinazolin-4-yl)phenyl]terephthalamic acid hydrate can be produced by dissolving methyl N-[3-(6,7-dimethoxy-2-methylaminoquinazolin-4-yl)phenyl]terephthalamic acid in acetone at room temperature or under heating and slowly cooling the solution to 4° C. to room temperature to precipitate crystals from the solution.

The amount of acetone used can be appropriately selected, provided that the lower limit is the amount that enables the dissolution of methyl N-[3-(6,7-dimethoxy-2-methylaminoquinazolin-4-yl)phenyl]terephthalamic acid by heating and the upper limit is the amount that does not decrease the yield of the crystals significantly.

The heating temperature can be appropriately selected from the temperatures which enable methyl N-[3-(6,7-dimethoxy-2-methylaminoquinazolin-4-yl)phenyl]terephthalamic acid to be dissolved in acetone, but preferably the heating temperature is 50° C. to the reflux temperature of the solvent for recrystallization. The rate of slow cooling can be 5 to 30° C./hour.

More particularly, the first crystals of methyl N-[3-(6,7-dimethoxy-2-methylaminoquinazolin-4-yl)phenyl]terephthalamic acid hydrate can be produced by the method described in Example 4 below.

The second crystals of methyl N-[3-(6,7-dimethoxy-2-methylaminoquinazolin-4-yl)phenyl]terephthalamic acid hydrate can be produced by dissolving methyl N-[3-(6,7-dimethoxy-2-methylaminoquinazolin-4-yl)phenyl]terephthalamic acid in methanol and precipitating crystals from the solution.

More particularly, the second crystals of methyl N-[3-(6,7-dimethoxy-2-methylaminoquinazolin-4-yl)phenyl]terephthalamic acid hydrate can be produced by dissolving methyl N-[3-(6,7-dimethoxy-2-methylaminoquinazolin-4-yl)phenyl]terephthalamic acid in methanol at room temperature or under heating and slowly cooling the solution to 4° C. to room temperature to precipitate crystals from the solution. The amount of methanol used can be appropriately selected, provided that the lower limit is the amount that enables the dissolution of methyl N-[3-(6,7-dimethoxy-2-methylaminoquinazolin-4-yl)phenyl]terephthalamic acid by heating and the upper limit is the amount that does not decrease the yield of the crystals significantly.

The heating temperature can be appropriately selected from the temperatures which enable methyl N-[3-(6,7-dimethoxy-2-methylaminoquinazolin-4-yl)phenyl]terephthalamic acid to be dissolved in methanol, but preferably the heating temperature is 50° C. to the reflux temperature of the solvent for recrystallization. The rate of slow cooling can be 5 to 30° C./hour.

More particularly, the second crystals of methyl N-[3-(6,7-dimethoxy-2-methylaminoquinazolin-4-yl)phenyl]terephthalamic acid hydrate can be produced by the method described in Example 5 below.

The third crystals of methyl N-[3-(6,7-dimethoxy-2-methylaminoquinazolin-4-yl)phenyl]terephthalamic acid hydrate can be produced by dissolving methyl N-[3-(6,7-dimethoxy-2-methylaminoquinazolin-4-yl)phenyl]terephthalamic acid in tetrahydrofuran and precipitating crystals from the solution. More particularly, the third crystals of methyl N-[3-(6,7-dimethoxy-2-methylaminoquinazolin-4-yl)phenyl]terephthalamic acid hydrate can be produced by dissolving methyl N-[3-(6,7-dimethoxy-2-methylaminoquinazolin-4-yl)phenyl]terephthalamic acid in tetrahydrofuran at room temperature or under heating and slowly cooling the solution to 4° C. to room temperature to precipitate crystals from the solution. Upon crystallization, water can be added. The amount of tetrahydrofuran used can be appropriately selected, provided that the lower limit is the amount that enables the dissolution of methyl N-[3-(6,7-dimethoxy-2-methylaminoquinazolin-4-yl)phenyl]terephthalamic acid by heating and the upper limit is the amount that does not decrease the yield of the crystals significantly.

The heating temperature can be appropriately selected from the temperatures which enable methyl N-[3-(6,7-dimethoxy-2-methylaminoquinazolin-4-yl)phenyl]terephthalamic acid to be dissolved in tetrahydrofuran, but preferably the heating temperature is 50° C. to the reflux temperature of the solvent for recrystallization. The rate of slow cooling can be 5 to 30° C./hour.

When water is added, the amount of water used is preferably 0.1 to 10 times (v/w) the amount of methyl N-[3-(6,7-dimethoxy-2-methylaminoquinazolin-4-yl)phenyl]terephthalamic acid. More particularly, the third crystals of methyl N-[3-(6,7-dimethoxy-2-methylaminoquinazolin-4-yl)phenyl]terephthalamic acid hydrate can be produced by the method described in Example 6 below.

The amorphous substance of methyl N-[3-(6,7-dimethoxy-2-methylaminoquinazolin-4-yl)phenyl]terephthalamic acid can be produced by dissolving methyl N-[3-(6,7-dimethoxy-2-methylaminoquinazolin-4-yl)phenyl]terephthalamic acid in dimethyl sulfoxide and precipitating an amorphous substance from the solution. More particularly, the amorphous substance of methyl N-[3-(6,7-dimethoxy-2-methylaminoquinazolin-4-yl)phenyl]terephthalamic acid can be produced by dissolving methyl N-[3-(6,7-dimethoxy-2-methylaminoquinazolin-4-yl)phenyl]terephthalamic acid in dimethyl sulfoxide at room temperature or under heating and slowly cooling the solution to 4° C. to room temperature to precipitate an amorphous substance. When precipitating the amorphous substance, water can be added. The amount of dimethyl sulfoxide used can be appropriately selected, provided that the lower limit is the amount that enables the dissolution of methyl N-[3-(6,7-dimethoxy-2-methylaminoquinazolin-4-yl)phenyl]terephthalamic acid by heating and the upper limit is the amount that does not decrease the yield of the amorphous substance significantly.

The heating temperature can be appropriately selected from the temperatures which enable methyl N-[3-(6,7-dimethoxy-2-methylaminoquinazolin-4-yl)phenyl]terephthalamic acid to be dissolved in dimethyl sulfoxide, but preferably the heating temperature is 50° C. to the reflux temperature of the solvent for recrystallization. The rate of slow cooling can be 5 to 30° C./hour.

When water is added, the amount of water used is preferably 0.1 to 10 times (v/w) the amount of methyl N-[3-(6,7-dimethoxy-2-methylaminoquinazolin-4-yl)phenyl]terephthalamic acid. More particularly, the amorphous substance of methyl N-[3-(6,7-dimethoxy-2-methylaminoquinazolin-4-yl)phenyl]terephthalamic acid can be produced by the method described in Example 7 below.

Methyl N-[3-(6,7-dimethoxy-2-methylaminoquinazolin-4-yl)phenyl]terephthalamic acid used in the above described production processes can be in the form of an anhydride or hydrate, or any crystal or amorphous substance, or the mixture thereof.

The salt of methyl N-[3-(6,7-dimethoxy-2-methylaminoquinazolin-4-yl)phenyl]terephthalamic acid can be any type of salt, as long as it forms as a salt with methyl N-[3-(6,7-dimethoxy-2-methylaminoquinazolin-4-yl)phenyl]terephthalamic acid and is pharmacologically acceptable. Examples of such salts include inorganic acid salts, organic acid salts, inorganic basic salts, organic basic salts, acidic or basic amino acid salts. Hydrates of such salts are also included in the present invention.

Preferred examples of inorganic acid salts may include hydrochloride, hydrobromide, sulfate, nitrate and phosphate, and hydrochloride, hydrobromide, sulfate or phosphate is particularly preferred. Preferred examples of organic acid salts may include acetate, succinate, fumarate, maleate, tartrate, citrate, lactate, stearate, benzoate, methanesulfonate, ethanesulfonate, p-toluenesulfonate and benzenesulfonate, and methanesulfonate or p-toluenesulfonate is particularly preferred.

Preferred examples of inorganic basic salts may include alkaline metal salts such as sodium salt or potassium salt; alkaline-earth metal salts such as calcium salt or magnesium salt; aluminum salt; and ammonium salt, and preferred examples of organic basic salts may include diethylamine salt, diethanolamine salt, meglumine salt, and N,N'-dibenzylethylenediamine salt.

Preferred examples of acidic amino acid salts may include aspartate and glutamate, and preferred examples of basic amino acid salts may include arginine salt, lysine salt and ornithine salt.

The salt of methyl N-[3-(6,7-dimethoxy-2-methylaminoquinazolin-4-yl)phenyl]terephthalamic acid or hydrate thereof can be produced by dissolving N-[3-(6,7-dimethoxy-2-methylaminoquinazolin-4-yl)phenyl]terephthalamic acid and a specified acid or base in a solvent methyl and precipitating a salt from the solution. More particularly, the salt of methyl N-[3-(6,7-dimethoxy-2-methylaminoquinazolin-4-yl)phenyl]terephthalamic acid or hydrate thereof can be produced by mixing methyl N-[3-(6,7-dimethoxy-2-methylaminoquinazolin-4-yl)phenyl]terephthalamic acid and a solvent at room temperature or under heating, adding a specified acid or base to the solution and dissolving the same in the solution, and slowly cooling the solution to 4° C. to room temperature to precipitate a salt.

The solvent used can be any solvent as long as it can dissolve methyl N-[3-(6,7-dimethoxy-2-methylaminoquinazolin-4-yl)phenyl]terephthalamic acid and the specified acid or base, but dimethyl sulfoxide is preferred. The amount of the solvent used is not particularly limited and can be appropriately selected, provided that the lower limit is the amount that enables the dissolution of methyl N-[3-(6,7-dimethoxy-2-methylaminoquinazolin-4-yl)phenyl]terephthalamic acid by heating and the upper limit is the amount that does not decrease the yield of the salt significantly.

The heating temperature can be appropriately selected from the temperatures which enable methyl N-[3-(6,7-dimethoxy-2-methylaminoquinazolin-4-yl)phenyl]terephthalamic acid to be dissolved in the solvent, but preferably the heating temperature is 50° C. to the reflux temperature of the solvent for recrystallization. The rate of slow cooling can be 5 to 30° C./hour.

The amount of the acid or base used can be 0.1 to 10 equivalent of methyl N-[3-(6,7-dimethoxy-2-methylaminoquinazolin-4-yl)phenyl]terephthalamic acid. More particularly, the salt of methyl N-[3-(6,7-dimethoxy-2-methylaminoquinazolin-4-yl)phenyl]terephthalamic acid or hydrate thereof can be produced by the method described in Examples 9 to 14 below.

Methyl N-[3-(6,7-dimethoxy-2-methylaminoquinazolin-4-yl)phenyl]terephthalamic acid used in the above described production process can be in the form of an anhydride or hydrate, or a crystal or amorphous substance, or the mixture thereof.

When the crystals, amorphous substance, salt or hydrate of salt of the present invention is to be used as a medicament, the crystals, amorphous substance, salt or hydrate of salt of the present invention is normally compounded with suitable pharmaceutical ingredients to prepare pharmaceutical products for use. Notwithstanding, the use of a drug substance form of the crystals, amorphous substance, salt or hydrate of salt of the present invention as a medicament should not be negated.

The pharmaceutical ingredients may include excipients, binders, lubricants, disintegrating agents, coloring agents, taste correctives, emulsifiers, surfactants, dissolving aids, suspending agents, isotonizing agents, buffering agents, preservatives, antioxidants, stabilizers, absorption enhancers, and the like, all of which are generally used in medicaments. If desired, these agents may be combined for use.

The excipients may include, for example, lactose, white soft sugar, glucose, corn starch, mannitol, sorbitol, starch, alpha starch, dextrin, crystalline cellulose, light silicic anhydride, aluminum silicate, calcium silicate, magnesium aluminometasilicate, calcium hydrogenphosphate, and the like.

The binders may include, for example, polyvinyl alcohol, methylcellulose, ethylcellulose, gum Arabic, tragacanth, gelatin, shellac, hydroxypropylmethylcellulose, hydroxypropylcellulose, carboxymethylcellulose sodium, polyvinylpyrrolidone, macrogol, and the like.

The lubricants may include, for example, magnesium stearate, calcium stearate, sodium stearyl fumarate, talc, polyethylene glycol, colloidal silica, and the like.

The disintegrating agents may include, for example, crystalline cellulose, agar, gelatin, calcium carbonate, sodium hydrogencarbonate, calcium citrate, dextrin, pectin, low-substituted hydroxypropylcellulose, carboxymethylcellulose, carboxymethylcellulose calcium, croscarmellose sodium, carboxymethyl starch, carboxymethyl starch sodium, and the like.

The coloring agents may include iron sesquioxide, yellow iron sesquioxide, carmine, caramel, beta-carotene, titanium oxide, talc, riboflavin sodium phosphate, yellow aluminum lake, and the like, which have been approved as additives for medicaments.

The taste correctives agents may include cocoa powder, menthol, aromatic powder, mentha oil, borneol, powdered cinnamon bark, and the like The emulsifiers or the surfactants may include stearyl triethanolamine, sodium lauryl sulfate, lauryl aminopropionic acid, lecithin, glycerin monostearate, sucrose fatty acid ester, glycerin fatty acid ester, and the like.

The dissolving aids may include polyethylene glycol, propylene glycol, benzyl benzoate, ethanol, cholesterol, triethanolamine, sodium carbonate, sodium citrate, Polysorbate 80, nicotinamide, and the like.

The suspending agents may include, in addition to the surfactants, hydrophilic polymers such as polyvinyl alcohol, polyvinylpyrrolidone, methylcellulose, hydroxymethylcellulose, hydroxyethylcellulose, and hydroxypropylcellulose.

The isotonizing agents may include glucose, sodium chloride, mannitol, sorbitol and the like.

The buffering agents may include the buffers of phosphate, acetate, carbonate, citrate and the like.

The preservatives may include methylparaben, propylparaben, chlorobutanol, benzyl alcohol, phenethyl alcohol, dehydroacetic acid, sorbic acid and the like.

The antioxidants may include sulfite, ascorbic acid, alpha-tocopherol and the like.

The stabilizers may include those generally used in medicaments.

The absorption enhancers may include those generally used in medicaments.

The pharmaceutical products described above may include: oral agents such as tablets, powders, granules, capsules, syrups, troches, and inhalations; external preparations such as suppositories, ointments, ophthalmic ointments, tapes, ophthalmic solutions, nasal drops, ear drops, poultices, and lotions; and injections. A preferred formulation is an external preparation, which directly acts on affected area.

The oral agents may appropriately be combined with the auxiliaries described above to form preparations. In addition, the surfaces of the agents may be coated if necessary.

The external preparations may appropriately be combined with the auxiliaries, in particular, excipients, binders, taste correctives, emulsifiers, surfactants, dissolving aids, suspending agents, isotonizing agents, preservatives, antioxidants, stabilizers, or absorption enhancers to form the preparations.

The injections may appropriately be combined with the auxiliaries, in particular, emulsifiers, surfactants, dissolving aids, suspending agents, isotonizing agents, preservatives, antioxidants, stabilizers, or absorption enhancers to form the preparations.

The dosage of the pharmaceutical of the present invention is different depending on the degree of symptoms, age, sex, body weight, dosage form, the type of salts, difference in sensitivity to the agent, the specific type of disease, or the like. In general, in the case of oral administration, the dosage of the pharmaceutical of the present invention is between approximately 30 μg and 10 g (preferably between 0.1 mg and 100 mg) of the crystals, amorphous substance, salt or hydrate of salt per adult per day. In the case of an external preparation, it is between 30 μg and 20 g (preferably between 100 μg and 10 g) of the crystals, amorphous substance, salt or hydrate of salt per adult per day. In the case of an injection, it is between 30 μg and 1 g (preferably between 100 μg and 500 mg) of the crystals, amorphous substance, salt or hydrate of salt per adult per day. The aforementioned dosage is used per day as a single administration, or divided over 2 to 6 administrations.

The crystals, amorphous substance, salt or hydrate of salt of the invention may be produced by the methods described by the following production examples and examples. However, these specific examples are merely illustrative and the compounds of the invention are in no way restricted by these specific examples.

The measurement of X-ray powder diffraction patterns was carried out according to the X-ray powder diffraction measurement method described in General Tests in the Japanese Pharmacopoeia, under the following conditions.

(Apparatus)

Rigaku X-ray DTA System: RINT-2000 (manufactured by Rigaku Corporation)

(Operation Method)

A sample was ground in an agate mortar, and then sampled on a copper board. Thereafter, measurement was carried out under the following conditions.

X-ray used: CuKα ray

Tube voltage: 40 kV

Tube current: 200 mA

Divergent slit: 0.3 mm

Scattering slit: ½ deg

Scanning rate: 2°/min

Scanning step: 0.02°

Scanning range (2θ): 5° to 40°

PRODUCTION EXAMPLE 1

Synthesis of 3-(2-chloro-6,7-dimethoxy-quinazolin-4-yl)phenylamine

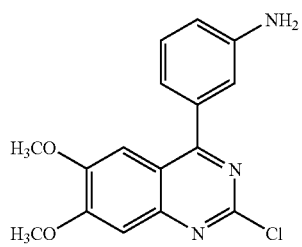 [SMILES: COc1cc2nc(Cl)nc(-c3cccc(N)c3)c2cc1OC]

Twenty-five grams of 2,4-dichloro-6,7-dimethoxyquinazoline was suspended in 2.25 L of a mixed solution consisting of toluene:tetrahydrofuran:a 2 N sodium carbonate solution=1:1:1. To the reaction mixture was added 21.5 g of 3-aminophenyl boronic acid ½ sulfate, and the mixture was degassed, the atmosphere in the reaction vessel was replaced with nitrogen. To the reaction mixture was added 2.23 g of tetrakis(triphenylphosphine)palladium(0), followed by stirring at 60° C. under a nitrogen atmosphere. Eighteen hours after initiation of the reaction, 1.2 g of tetrakis(triphenylphosphine)palladium(0) was added to the reaction mixture, and the stirring was continued. Thirty hours later, 1.2 g of tetrakis(triphenylphosphine)palladium(0) was further added to the reaction mixture, and stirring was further continued. Forty-eight hours after initiation of the reaction, the reaction mixture was cooled, and it was then transferred into a separatory funnel, so as to separate an organic layer. The obtained organic layer was washed with 300 mL of brine, and was then dried over anhydrous magnesium sulfate. The desiccant was removed by passing it through 250 g of silica gel. The silica gel was washed with 1.5 L of ethyl acetate, and the obtained organic layers were combined and concentrated to dryness. The residue was triturated with 200 mL of ethyl acetate, and the obtained solid was then filtrated. The solid was washed with 100 mL of diethyl ether and 200 mL of a mixed solution consisting of n-heptane:ethyl acetate=1:1, and dried under aeration to yield 28.2 g of a target product. Yield: 92.5%

$^1$H-NMR (DMSO-d$_6$) δ (ppm): 3.86 (3H, s), 4.01 (3H, s), 5.40 (2H, br), 6.79 (1H, dd, J=1.6, 8.0 Hz), 6.93 (1H, brd, J=8.0 Hz), 7.02 (1H, t, J=1.6 Hz), 7.24 (1H, t, J=8.0 Hz), 7.41 (1H, s), 7.43 (1H, s).

PRODUCTION EXAMPLE 2

Synthesis of [4-(3-aminophenyl)-6,7-dimethoxyquinazolin-2-yl]methylamine

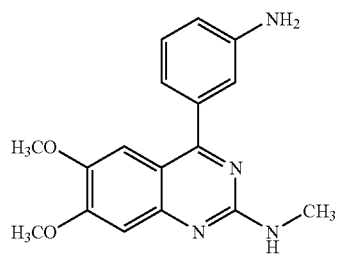 [SMILES: CNc1nc(-c2cccc(N)c2)c2cc(OC)c(OC)cc2n1]

Fourteen grams of 3-(2-chloro-6,7-dimethoxyquinazolin-4-yl)phenylamine was suspended in 135 mL of a mixed solution consisting of tetrahydrofuran:isopropanol=2:1. To the reaction mixture was added 89 mL of a methylamine solution in methanol, and the reaction mixture was stirred in a pressure-resistant sealed tube reactor at 130° C. for 24 hours. After the reaction mixture was allowed to cool down to room temperature, it was diluted with 300 mL of ethyl acetate and then washed with 300 mL of water. A water layer was extracted with 100 mL of ethyl acetate, and the combined organic layer was washed with 100 mL of brine. The organic layer was separated and was then dried over anhydrous magnesium sulfate. The desiccant was removed by filtration, the organic layer was concentrated to dryness, and the resultant was triturated with a mixed solvent consisting of ethyl acetate:tetrahydrofuran=3:1. The obtained solid was filtrated, and the filtrate was then washed with ethyl acetate, and dried under aeration to yield 10 g of a target product. The filtrate was adsorbed on a 50 g silica gel column, and it was then eluted with a mixed solution consisting of ethyl acetate:methanol=9:1, and the eluent was concentrated to dryness. The residue was triturated with ethyl acetate, and the obtained solid was then filtrated. The solid was washed with diethyl ether, and dried under aeration to yield 1.4 g of a target product. Total yield: 82.9%

$^1$H-NMR (CDCl$_3$) δ (ppm): 3.12 (3H, d, J=5.2 Hz), 3.80 (2H, brs), 3.82 (3H, s), 4.03 (3H, s), 5.30 (1H, br), 6.83 (1H, dd, J=1.6, 8.0 Hz), 6.99 (1H, t, J=1.6 Hz), 7.04 (1H, brd, J=8.0 Hz), 7.07 (1H, s), 7.15 (1H, s), 7.30 (1H, t, J=8.0 Hz).

PRODUCTION EXAMPLE 3

Alternative method for synthesis of 3-(2-chloro-6,7-dimethoxy-quinazolin-4-yl)phenylamine (production example 1e To 634 g of sodium carbonate (5.98 mol) was added 2.91 kg of water under a nitrogen atmosphere, followed by stirring for dissolution. To the solution were added 3.0 L of tetrahydrofuran, 431 g of 3-aminophenyl boronic acid monohydrate (2.78 mol), 30.4 g of triphenylphosphine (0.116 mol) and 26.0 g of dichloropalladium (0.116 mol) in this order. To the mixture was dropwise added a solution of 2,4-dichloro-6,7-dimethoxyquinazoline (600 g; 2.32 mol) in tetrahydrofuran (12.0 L) over 2 hours while stirring at 60° C., followed by stirring at the same temperature for 16 hours. To the mixture were added 3.0 kg of a 5% sodium chloride solution and 12.0 L of tetrahydrofuran in this order, and the mixture was stirred at 50° C. for 1 hour and allowed to cool down to 25° C. The mixture was filtered through celite to remove the insoluble matter, and the filtrate was transferred to separatory funnel and the organic layer was separated. To the organic layer were added 150 g of anhydrous magnesium sulfate and 60.0 g of activated carbon, and the mixture was stirred at 50° C. for 1 hour and allowed to cool down to 25° C. The mixture was filtered through celite to remove the insoluble matter, and the filtrate was concentrated under reduced pressure. To the residue was added 6.0 L of water, and the mixture was stirred at room temperature for 1 hour. The precipitated crystals were filtered, and the crystals were dried at 50° C. under reduced pressure to yield 730 g of a target product. Yield: 62.1%

PRODUCTION EXAMPLE 4

Alternative method for synthesis of [4-(3-aminophenyl)-6,7-dimethoxyquinazolin-2-yl]methylamine (production example 2)

Two hundred grams of crude 3-(2-chloro-6,7-dimethoxyquinazolin-4-yl)phenylamine (content 124 g; 0.394 mol) was suspended in a mixed solution of 1.2 L of tetrahydrofuran and 0.6 L of isopropanol. To the mixture was added 1.2 L of a methylamine solution in methanol, and the mixture was stirred in a SUS autoclave at 90° C. for 15 hours. The reaction mixture was allowed to cool down to 25° C., and concentrated under reduced pressure. To the residue were added 1.0 L of water and 4.0 L of chloroform, and the mixture was stirred at 50° C. for 0.5 hours and allowed to cool down to 25° C. The mixture was filtered through celite to remove the insoluble matter, and the filtrate was transferred to separatory funnel and the organic layer was separated. To the organic layer were added 50.0 g of anhydrous magnesium sulfate and 20.0 g of activated carbon, and the mixture was stirred at 50° C. for 1 hour and allowed to cool down to 25° C. The mixture was filtered through celite to remove the insoluble matter, and the filtrate was concentrated under reduced pressure. To the residue was added 904 mL of chloroform, and the mixture was stirred at 50° C. for 1 hour and stirred overnight after turning off the heater. Then the mixture was stirred in an ice bath for 2 hours and precipitated crystals were filtered, and the crystals were dried at 50° C. under reduced pressure to yield 76.3 g of a target product. Yield: 38.7%

PRODUCTION EXAMPLE 5

Synthesis of methyl N-[3-(6,7-dimethoxy-2-methylaminoquinazolin-4-yl)phenyl]terephthalamic acid

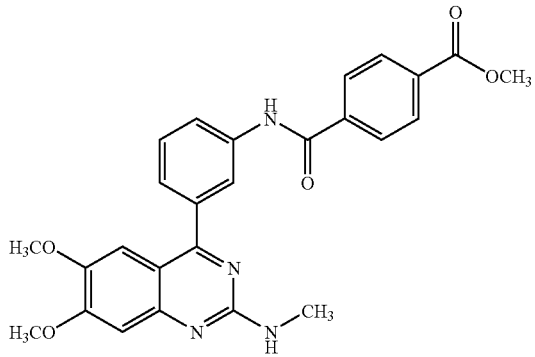 [SMILES: CNc1nc(-c2cccc(NC(=O)c3ccc(C(=O)OC)cc3)c2)c2cc(OC)c(OC)cc2n1]

(1) Preparation of "Terephthalic Acid Monomethyl Ester Chloride/N,N-diisopropylethylamine" Solution A suspension of 1.997 kg (11.08 mol) of terephthalic acid monomethyl ester in 15.60 kg of 1,2-dimethoxyethane was stirred in a nitrogen atmosphere while being cooled at 10° C. To the suspension was added 400 mL (5.17 mol) of N,N-dimethylformamide and 1.323 kg (10.56 mol) of thionyl chloride in this order, and then the container was washed with 1.00 L of 1,2-dimethoxyethane. The suspension was stirred under heating at 60 to 73° C. for 1 hour and 2 minutes and then stirred while being cooled. 1.36 kg (10.52 mol) of N,N-diisopropylethylamine was added dropwise to the solution while cooling at 0° C., and the container was washed with 1.00 L of 1,2-dimethoxyethane. Then the reaction solution was stirred at 25° C., and the stirring was stopped 38 minutes after the internal temperature had reached 20° C. The reaction mixture was transferred into a plastic container, and 22.00 kg of "monomethyl terephthalate chloride/N,N-diisopropylethylamine" solution (terephthalic acid monomethyl ester chloride content: 1.84 kg) was obtained as a slightly tannish solution.

(2) Synthesis of methyl N-[3-(6,7-dimethoxy-2-methylaminoquinazolin-4-yl)phenyl]terephthalamic acid A suspension of 2.000 kg (6.39 mol) of [4-(3-aminophenyl)-6,7-dimethoxyquinazolin-2-yl]methylamine in 71.14 kg of tetrahydrofuran was stirred in a nitrogen atmosphere while being cooled at 0° C. To the suspension was added dropwise 16.70 kg of "monomethyl terephthalate chloride/N,N-diisopropylethylamine" solution (monomethyl terephthalate chloride content: 1.40 kg, 7.03 mol) over 1 hour and 26 minutes, and the container was washed with 1.40 L of 1,2-dimethoxyethane. The mixture was stirred at 0° C. for 13 hours and 4 minutes. Under cooling at 0° C., 36.5 kg of ethyl acetate was added to the reaction mixture and then 80.1 kg of a 5% aqueous solution of sodium hydrogencarbonate was added dropwise, and the mixture was stirred at 20° C. for 1 hour and 10 minutes. Then, 37.3 kg of ethyl acetate was added into the mixture, the mixture was stirred, and the water layer was separated. The organic layer was washed with 40.0 kg of a 5% aqueous solution of sodium chloride, 40.2 kg of water, and 40.1 kg of water in this order. The organic layer was concentrated under reduced pressure at a jacket temperature of 40° C., 23.70 kg of methanol was added to the residue, and stirred for 1 hour and 1 minute while being heated to 60 to 66° C. 23.60 kg of 2-propanol was added dropwise to the suspension over 1 hour while stirring the suspension at a jacket temperature of 50° C. Then, the suspension was cooled at a cooling rate of 10° C./hour and stirred at 20° C. for 12 hours and 23 minutes. The precipitated crystals were filtered, rinsed with a mixed solution of 3.00 L of methanol and 3.00 L of 2-propanol and 6.00 L of 2-propanol in this order to yield 5.52 kg of a crude product (content of the target compound: 2.57 kg, 5.44 mol) as pale yellow crystals (yield: 85.3%).

In a nitrogen atmosphere, a suspension of 5.398 kg of the crude product (content of the target compound: 2.518 kg, 5.33 mol) in 8.01 L of dimethyl sulfoxide was stirred under heating at 60 to 70° C., and the crystals were dissolved. The solution was filtered, and rinsed with 2.00 L of dimethyl sulfoxide. The filtrate was transferred into a 210 L reaction vessel having been heated at 60° C. and washed with 2.01 L of dimethyl sulfoxide. To the solution, 18.9 kg of 2-propanol was added dropwise over 40 minutes, 15.02 g of crystals of the target compound was seeded, and 9.44 kg of 2-propanol was added dropwise over 57 minutes. After stirring the suspension at 60° C. for 1 hour and 30 minutes, the jacket temperature was set at 80° C. and the stirring was continued for 37 hours and 24 minutes. Then, 56.6 kg of 2-propanol was added dropwise to the suspension over 2 hours and 8 minutes, the mixture was cooled to 20° C. at a cooling rate of 10° C./hour and stirred at the same temperature for 65 hours and 50 minutes. The precipitated crystals were filtered, rinsed with a mixed solution of 534 mL of dimethyl sulfoxide and 4.81 L of 2-propanol and 8.01 L of 2-propanol in this order. The crystals were dried under reduced pressure at 50° C. to yield 2.30 kg of the target product as yellow crystals (yield 90.8%).

EXAMPLE 1

Synthesis of methyl N-[3-(6,7-dimethoxy-2-methylaminoquinazolin-4-yl)phenyl]terephthalamic acid

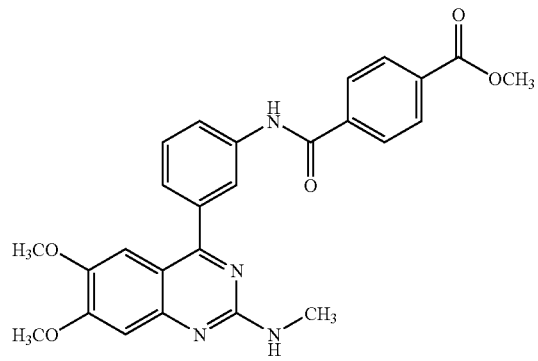 [SMILES: CNc1nc(-c2cccc(NC(=O)c3ccc(C(=O)OC)cc3)c2)c2cc(OC)c(OC)cc2n1]

To a solution of 16.8 g of [4-(3-aminophenyl)-6,7-dimethoxyquinazolin-2-yl]methylamine and 8.6 g of pyridine dissolved in 300 mL of tetrahydrofuran was added 11.8 g of 4-chlorocarbonylbenzoic acid methyl ester at room temperature, followed by stirring for 24 hours. To the reaction mixture was added 100 mL of dimethyl sulfoxide, the mixture was partitioned between a mixed solvent consisting of 2,000 mL of ethyl acetate and 1,000 mL of tetrahydrofuran, and 1,000 mL of a saturated sodium hydrogencarbonate solution, and the organic layer was separated. The water layer was further extracted with a mixed solvent consisting of 500 mL of ethyl acetate and 500 mL of tetrahydrofuran. The combined organic layer was then washed with 1,000 mL of a saturated sodium hydrogencarbonate solution and 1,000 mL of brine in this order, and dried over anhydrous magnesium sulfate. The desiccant was removed by filtration with 100 g of a basic silica gel pad, followed by well washing with 2,000 mL of ethyl acetate. The combined eluent was concentrated under reduced pressure, and the obtained crude product was suspended and triturated in a mixed solvent consisting of 100 mL of tetrahydrofuran and 500 mL of diethyl ether. The precipitated crystals were collected by filtration, washed twice with 100 mL of diethyl ether, and dried under aeration at 50° C. for 5 hours to yield 13.8 g of the crystals of the titled compound (yield: 53.2%).

$^1$H-NMR (DMSO-$d_6$) δ (ppm): 2.88 (3H, d, J=4.4 Hz), 3.74 (3H, s), 3.89 (3H, s), 3.92 (3H, s), 6.99 (1H, s), 7.00 (1H, brs), 7.17 (1H, s), 7.46 (1H, d, J=8.0 Hz), 7.55 (1H, t, J=8.0 Hz), 7.87 (1H, brd, J=8.0 Hz), 8.08 (4H, s), 8.20 (1H, brs), 10.61 (1H, s).

EXAMPLE 2

Anhydrous crystals 1 of methyl N-[3-(6,7-dimethoxy-2-methylaminoquinazolin-4-yl)phenyl]terephthalamic acid (Example 1)

To 75.28 mg of the compound obtained in Example 1 was added 9 mL of acetonitrile, and the mixture was heated in an oil bath for dissolution, and allowed to cool down to room temperature. The precipitate was collected by filtration, and dried at 50° C. overnight to yield the titled crystals.

The major X-ray diffraction angles (2θ) of the substance are 8.2°, 16.5° and 24.5°. FIG. 1 shows an X-ray diffraction pattern.

EXAMPLE 3

Anhydrous crystals 2 of methyl N-[3-(6,7-dimethoxy-2-methylaminoquinazolin-4-yl)phenyl]terephthalamic acid (Example 1)

To 52.93 mg of the compound obtained in Example 1 was added 12 mL of 2-propanol, and the mixture was heated in an oil bath for dissolution, and allowed to cool down to room temperature. The precipitate was collected by filtration, and dried at 50° C. overnight to yield the titled crystals.

Figure 2:
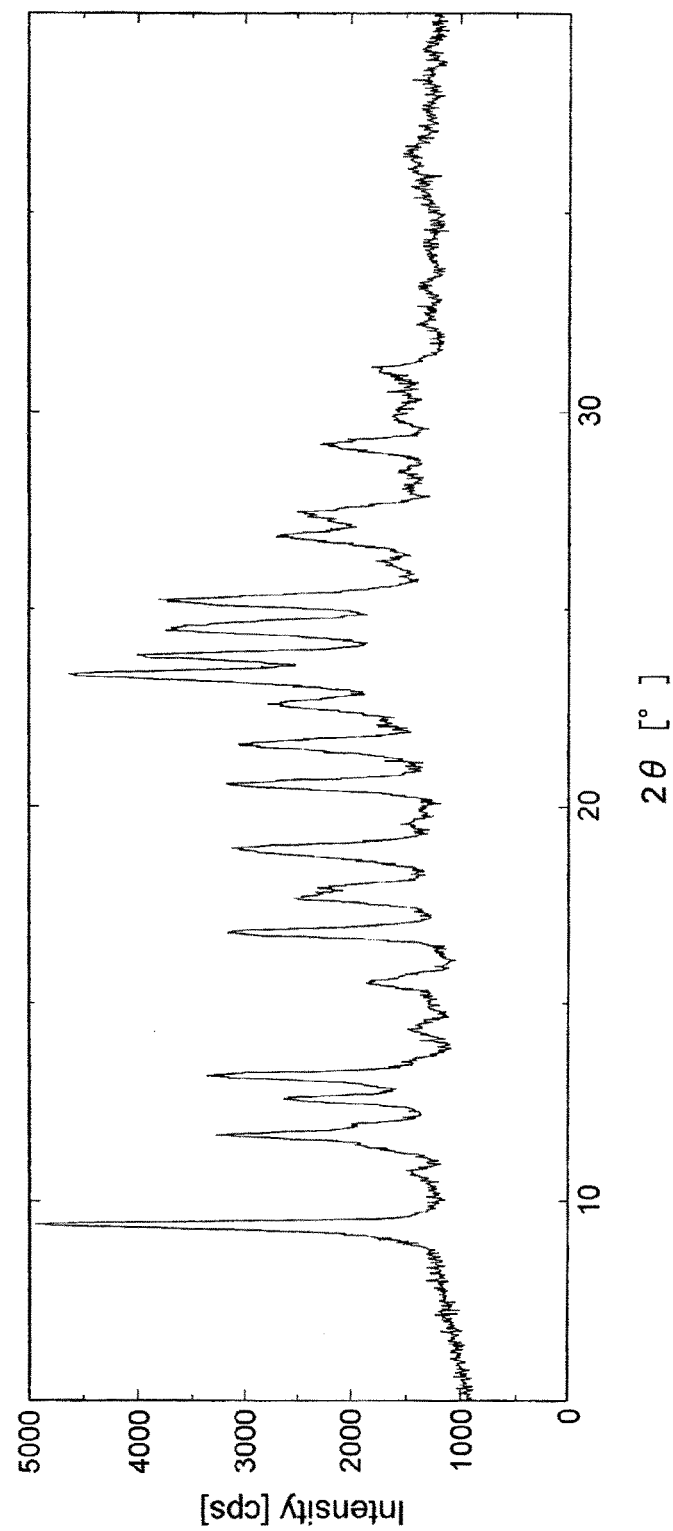
FIG. 2 shows an X-ray powder diffraction pattern for the crystals obtained in Example 3.

The major X-ray diffraction angles (2θ) of the substance are 9.4°, 16.8° and 23.3°. FIG. 2 shows an X-ray diffraction pattern.

EXAMPLE 4

Hydrate crystals 1 of methyl N-[3-(6,7-dimethoxy-2-methylaminoquinazolin-4-yl)phenyl]terephthalamic acid (Example 1)

To 75.71 mg of the compound obtained in Example 1 was added 15 mL of acetone, and the mixture was heated in an oil bath for dissolution, and allowed to cool down to room temperature. The precipitate was collected by filtration, and dried at 50° C. overnight to yield the titled crystals.

Figure 3:
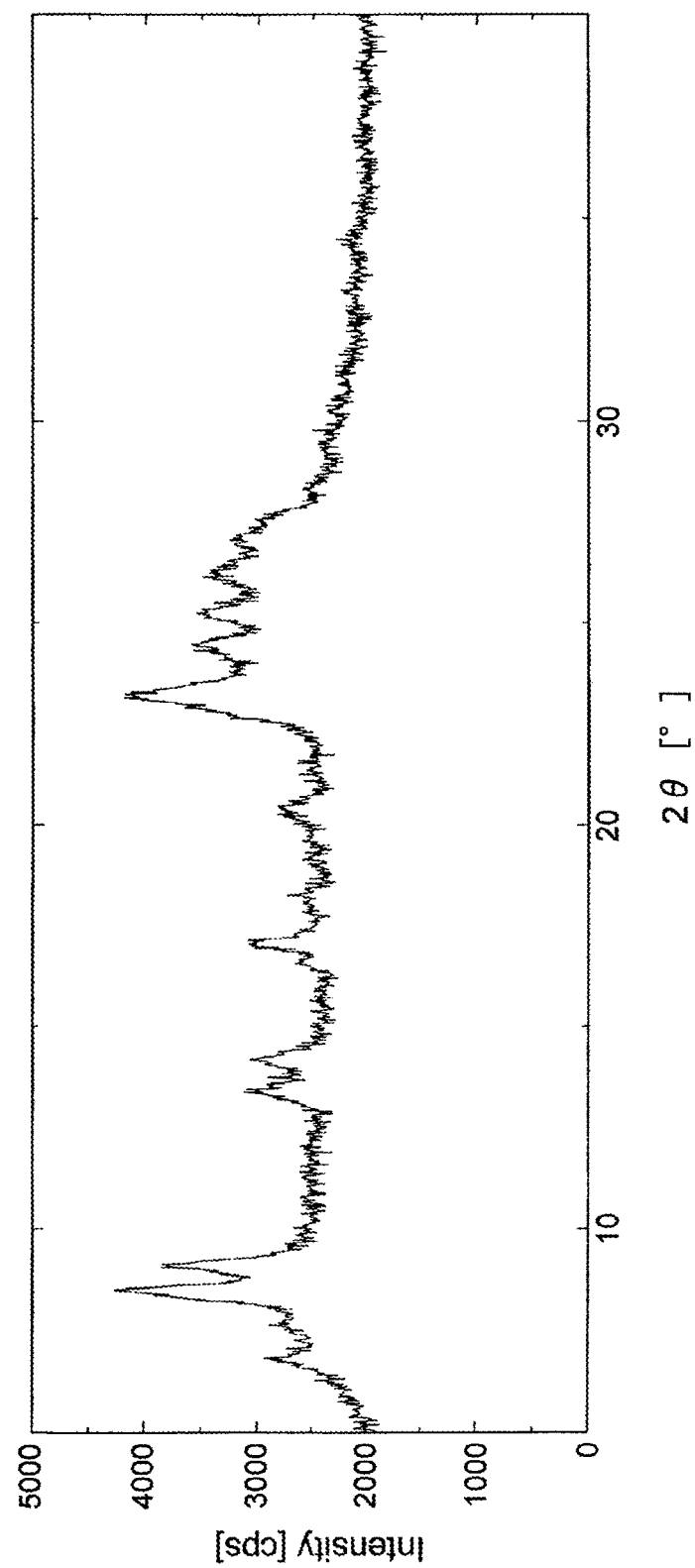
FIG. 3 shows an X-ray powder diffraction pattern for the crystals obtained in Example 4.

The major X-ray diffraction angles (2θ) of the substance are 8.6°, 9.1° and 23.2°. FIG. 3 shows an X-ray diffraction pattern.

EXAMPLE 5

Hydrate crystals 2 of methyl N-[3-(6,7-dimethoxy-2-methylaminoquinazolin-4-yl)phenyl]terephthalamic acid (Example 1)

To 75.88 mg of the compound obtained in Example 1 was added 16 mL of methanol, and the mixture was heated in an oil bath for dissolution, and allowed to cool down to room temperature. The precipitate was collected by filtration, and dried at 50° C. overnight to yield the titled crystals.

Figure 4:
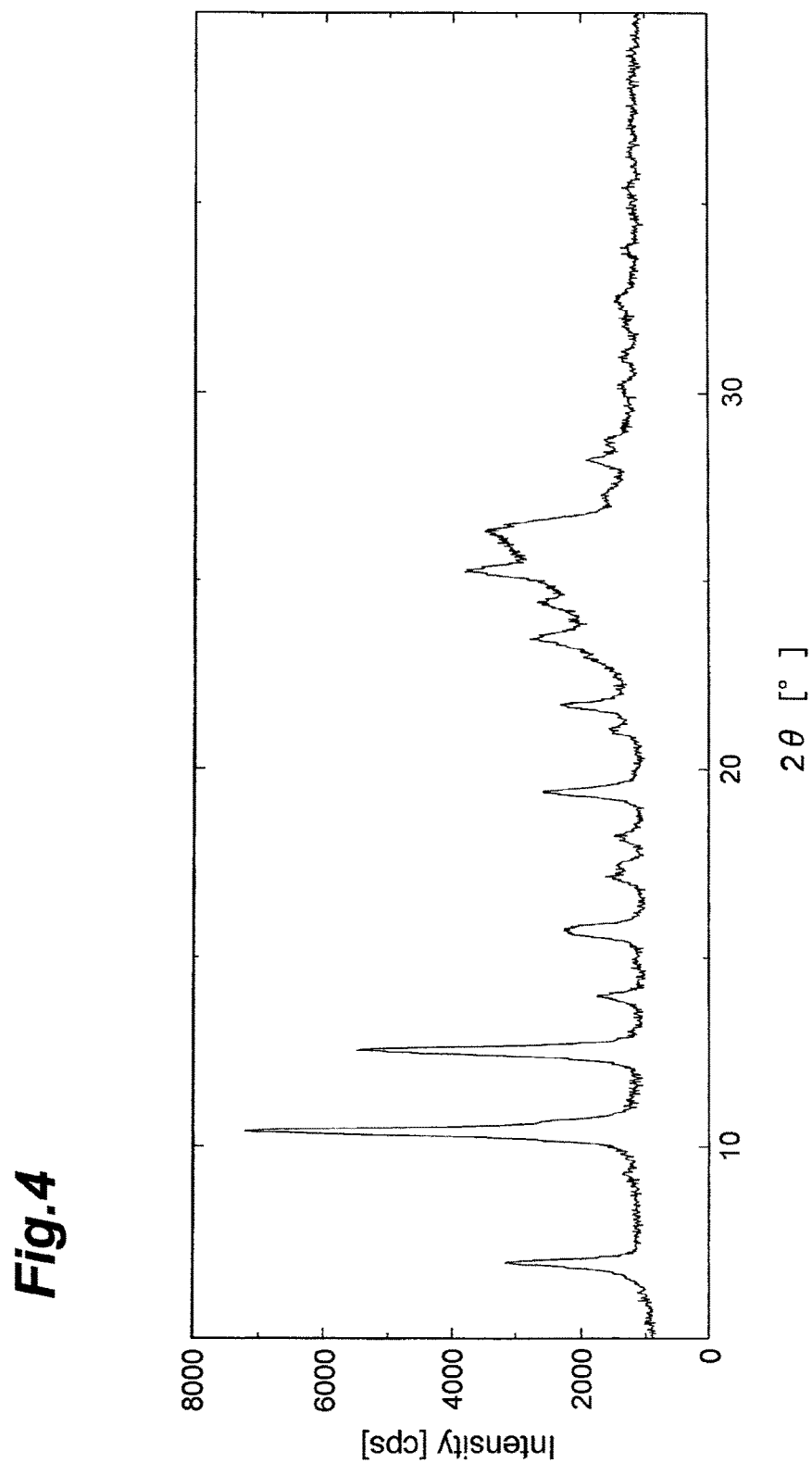
FIG. 4 shows an X-ray powder diffraction pattern for the crystals obtained in Example 5.

The major X-ray diffraction angles (2θ) of the substance are 7.0°, 10.4° and 12.6°. FIG. 4 shows an X-ray diffraction pattern.

EXAMPLE 6

Hydrate crystals 3 of methyl N-[3-(6,7-dimethoxy-2-methylaminoquinazolin-4-yl)phenyl]terephthalamic acid (Example 1)

To 49.90 mg of the compound obtained in Example 1 was added 2 mL of tetrahydrofuran, and the mixture was heated in an oil bath for dissolution, and allowed to cool down to room temperature. Thereafter, 10 mL of water was further added to the mixture, which was allowed to stand. The precipitate was collected by filtration, and dried at 50° C. overnight to yield the titled crystals.

Figure 5:
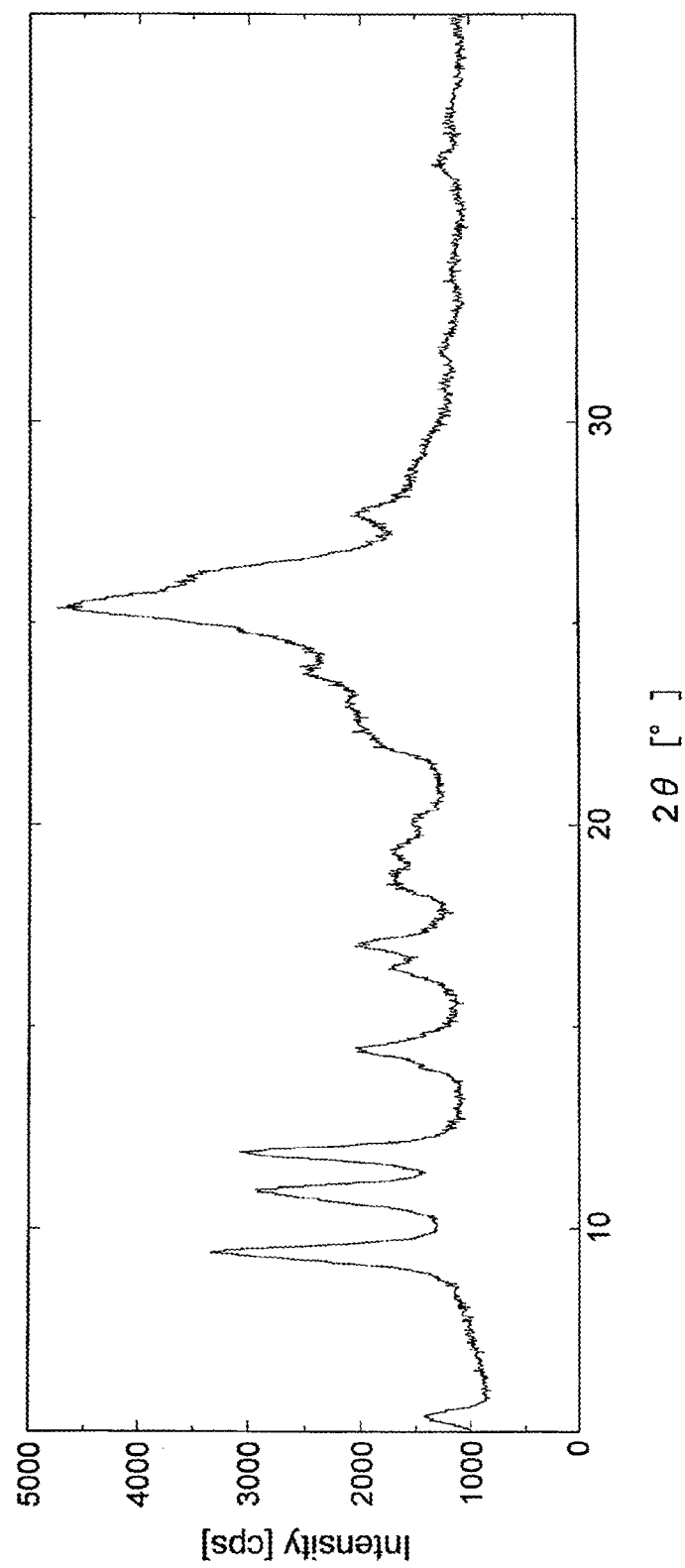
FIG. 5 shows an X-ray powder diffraction pattern for the crystals obtained in Example 6.

The major X-ray diffraction angles (2θ) of the substance are 5.4°, 10.9° and 11.9°. FIG. 5 shows an X-ray diffraction pattern.

EXAMPLE 7

Amorphous methyl N-[3-(6,7-dimethoxy-2-methylaminoquinazolin-4-yl)phenyl]terephthalamic acid (Example 1)

To 36.49 mg of the compound obtained in Example 1 was added 0.2 mL of dimethyl sulfoxide to dissolve the compound. Thereafter, 10 mL of water was further added to the mixture, which was allowed to stand. The precipitate was collected by filtration, and dried at 50° C. overnight to yield the titled amorphous substance.

Figure 6:
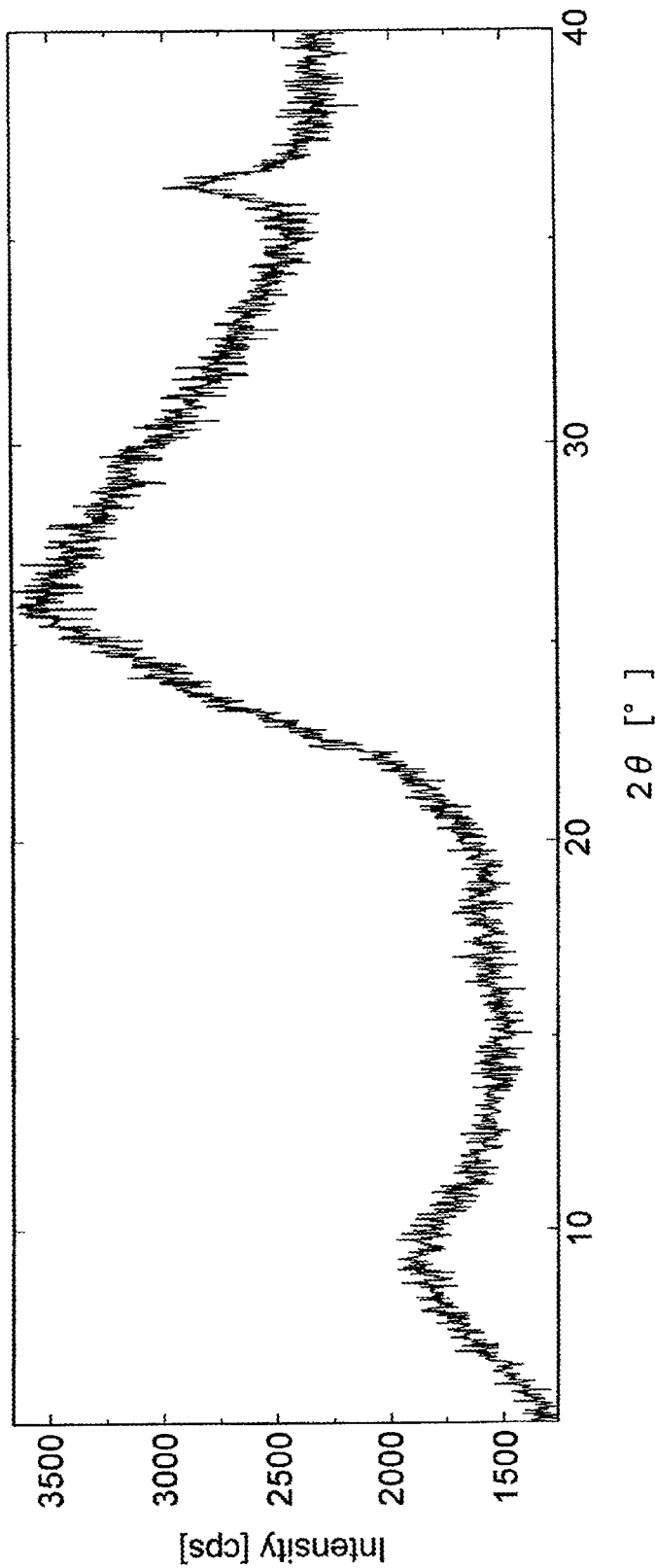
FIG. 6 shows an X-ray powder diffraction pattern for the amorphous substance obtained in Example 7.

FIG. 6 shows an X-ray diffraction pattern.

EXAMPLE 8

Alternative method for producing anhydrous crystals 1 of methyl N-[3-(6,7-dimethoxy-2-methylaminoquinazolin-4-yl)phenyl]terephthalamic acid (Example 1)

A suspension of 10.00 g (55.51 mmol) of monomethyl terephthalate in 90 mL of 1,2-dimethoxyethane was stirred, while it is cooled in a cold bath at 10° C. To the suspension were added 2.0 mL of N,N-dimethylformamide and 6.61 g (52.75 mmol) of thionyl chloride in this order, and the suspension was stirred at 60° C. to 65° C. for 1 hour. The mixture was cooled, and 6.83 g (52.82 mmol) of diisopropylethylamine was added dropwise to the mixture under cooling with ice bath. Subsequently, the reaction mixture was stirred at room temperature, and the stirring was stopped 30 minute after the internal temperature had reached 20° C. The reaction mixture was placed in a 200-mL flask to yield 109.49 g of [terephthalic acid monomethyl ester chloride/diisopropylethylamine] (the content of terephthalic acid monomethyl ester chloride: 8.89 g) as a slightly tannish solution.

Subsequently, a suspension of 9.50 g (30.00 mmol) of [4-(3-aminophenyl)-6,7-dimethoxyquinazolin-2-yl]methylamine in 380 mL of tetrahydrofuran was stirred, while it was cooled at 0° C. To the suspension was added dropwise over 1 hour, 80.71 g of the above mixed solution consisting of [terephthalic acid monomethyl ester chloride/diisopropylethylamine] (the content of terephthalic acid monomethyl ester chloride: 6.55 g; 33.00 mmol). The mixture was then stirred at 0° C. for 11 hours. Thereafter, 190 mL of ethyl acetate was added to the reaction mixture at 0° C., and 380 g of a 5% sodium hydrogencarbonate solution was then added dropwise. The reaction mixture was transferred into a separatory funnel, and 190 mL of ethyl acetate was added. After extraction, the organic layer was separated, and washed with 190 g of a 5% sodium chloride solution and 190 mL of water (twice) in this order. The organic layer was concentrated under reduced pressure at 40° C. To the residue was added 143 mL of methanol, and the mixture was stirred while heating to 40° C. Thirty-three minutes after initiation of stirring, the temperature of an oil bath was set at 75° C. Thereafter, 30 minutes after the internal temperature had exceeded 60° C., the oil bath was set at 50° C. When the internal temperature was decreased to 55° C., 143 mL of 2-propanol was added dropwise. Subsequently, the internal temperature was gradually cooled to 27.3° C., and the mixture was then stirred at 20° C. for 17 hours. The precipitated crystals were filtered, and rinsed with a mixed solution of 14.3 mL of methanol and 14.3 mL of 2-propanol to yield 15.72 g of a crude target product (wet body; the content of the target compound: 13.31 g) as pale yellow crystals (yield: 93.9%).

A suspension of 15.48 g of the crude product (the content of the a target product: 13.11 g; 27.00 mmol) in 40 mL of dimethyl sulfoxide was stirred under heating at 60° C., and the crystals were dissolved. The obtained solution was filtered, and washed with 10 mL of dimethyl sulfoxide. The filtrate was transferred into a 1,000-mL four-necked glass vessel, which had previously been heated with a 60° C. hot water jacket, and the residue was washed with 10 mL of dimethyl sulfoxide. The mixture was then stirred under heating at 60° C. Thereafter, 119 mL of 2-propanol was added dropwise to this solution, and 49.3 mg of the crystals of the target product was seeded in the mixture. Thereafter, 60 mL of 2-propanol was added dropwise to the mixture. This suspension was stirred at 60° C. for 2 hours, the temperature of the jacket was set at 80° C., and the suspension was continuously stirred for 16.5 hours. Subsequently, 120 mL of 2-propanol was added dropwise to the suspension, and 3 hours later, 362 mL of 2-propanol was further added dropwise. Thereafter, the mixture was gradually cooled to 20° C. at the cooling rate of 10° C./h, and it was then stirred at the same temperature. Fifty nine point five hours later, the precipitated crystals were filtered, and rinsed with a mixed solution of 2.6 mL of dimethyl sulfoxide and 24 mL of 2-propanol and 40 mL of 2-propanol in this order. The crystals were dried under reduced pressure to yield 9.84 g of a target product as yellow crystals (yield: 73.7%).

Figure 7:
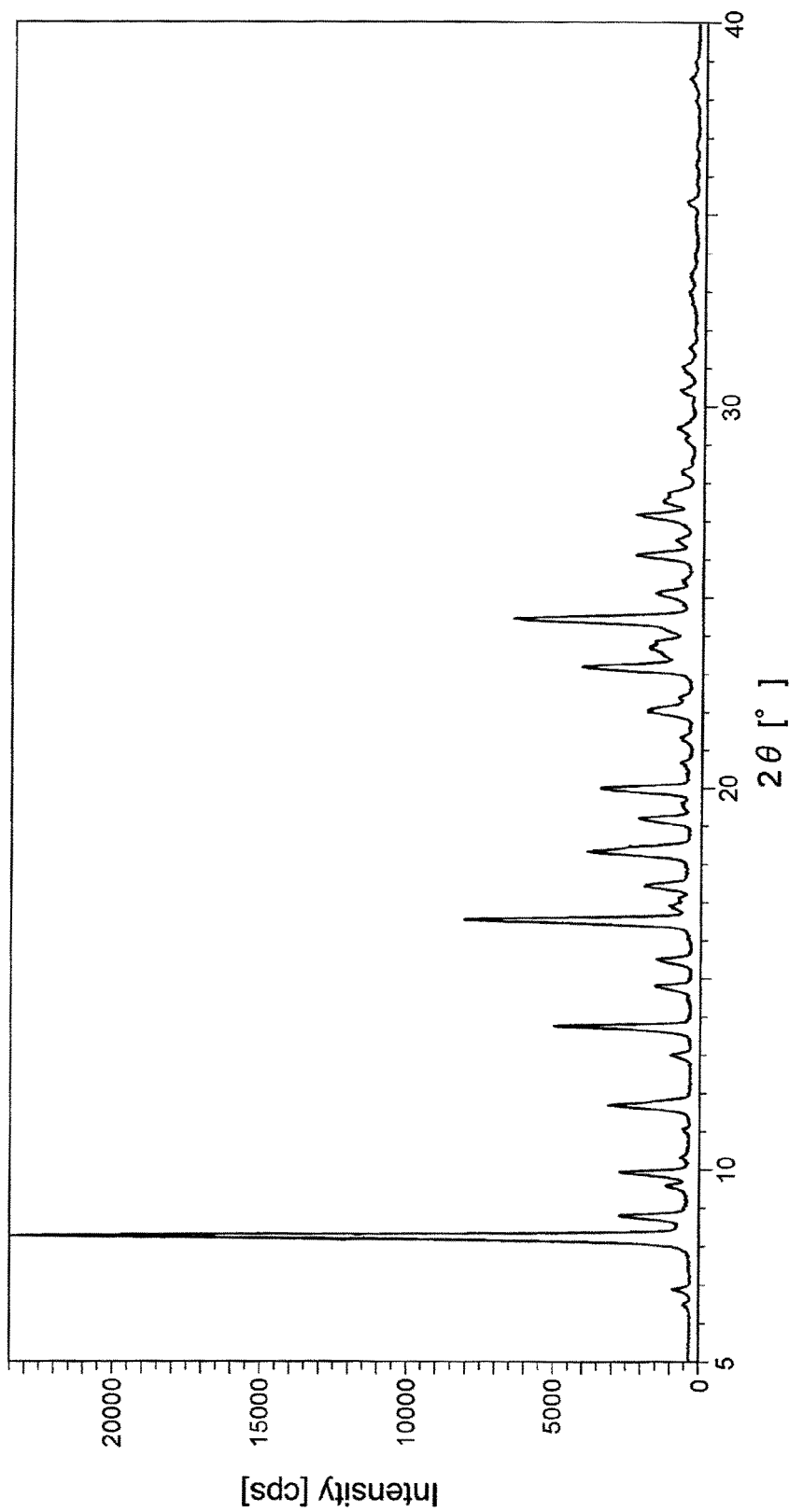
FIG. 7 shows an X-ray powder diffraction pattern for the crystals obtained in Example 8.

FIG. 7 shows an X-ray diffraction pattern.

EXAMPLE 9

Methyl N-[3-(6,7-dimethoxy-2-methylamino-quinazolin-4-yl)phenyl]terephthalamic acid hydrochloride Dimethyl sulfoxide (1 mL) and hydrochloric acid (22 μL) were added to methyl N-[3-(6,7-dimethoxy-2-methylamino-quinazolin-4-yl)phenyl]terephthalamic acid (99.37 mg). Dimethyl sulfoxide (2 mL) was added to and dissolved in the mixture while heating the mixture, 2-propanol (3 mL) was added to the mixture, and the mixture was cooled to room temperature to be solidified. The solid was collected by filtration to yield the titled compound (88.65 mg).

Figure 8:
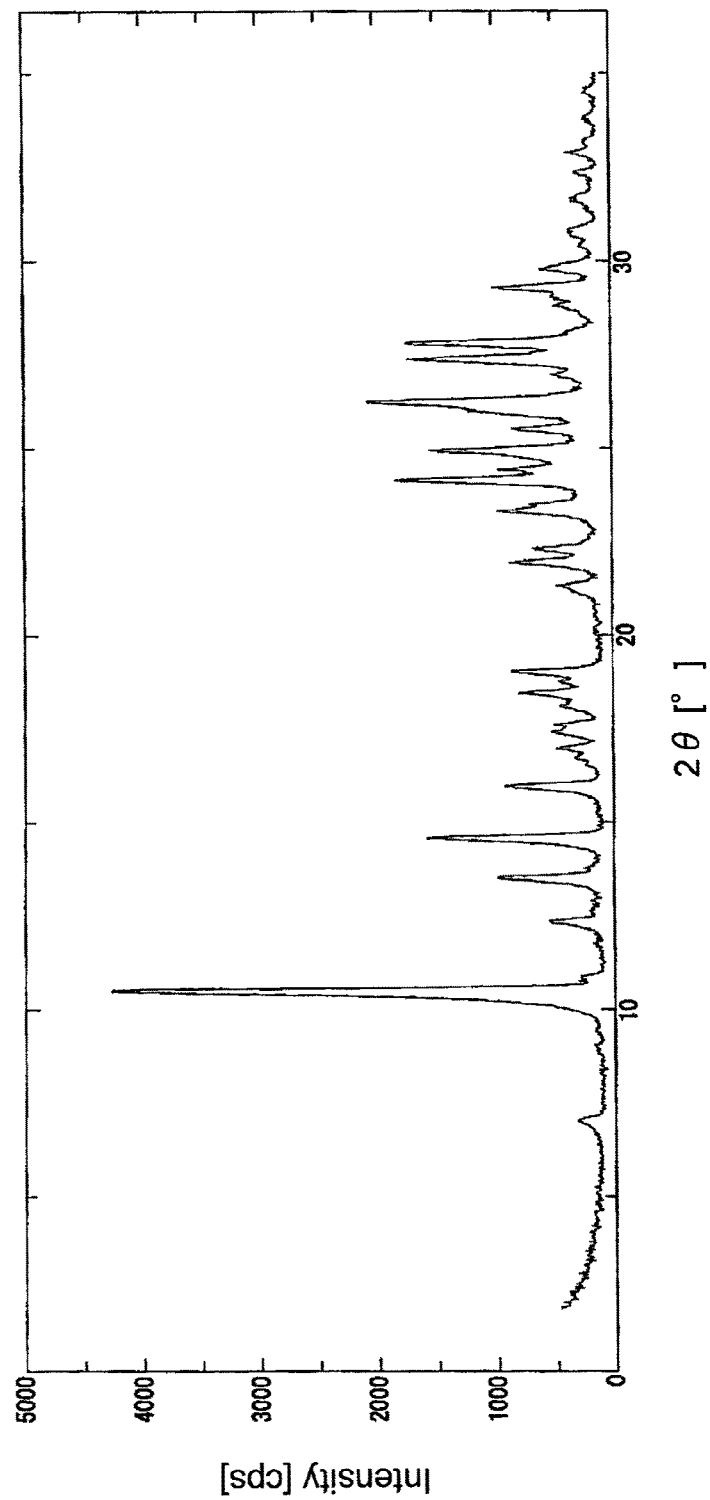
FIG. 8 shows an X-ray powder diffraction pattern for the hydrochloride obtained in Example 9.

X-ray diffraction data (diffraction angle (2θ)/relative intensity): 10.52°/100, 13.52°/23, 14.58°/38, 15.98°/22, 23.32°/23, 24.16°/43, 24.94°/37, 25.98°/29, 26.24°/49 and 27.38°/41. Of these peaks, particularly characteristic peaks were at 10.52° and 14.58°. FIG. 8 shows an X-ray diffraction pattern.

EXAMPLE 10

Methyl N-[3-(6,7-dimethoxy-2-methylamino-quinazolin-4-yl)phenyl]terephthalamic acid hydrobromide Dimethyl sulfoxide (1 mL) and hydrobromic acid (40 μL) were added to methyl N-[3-(6,7-dimethoxy-2-methylamino-quinazolin-4-yl)phenyl]terephthalamic acid (100.90 mg). 2-Propanol (5 mL) was added to the mixture while heating the mixture, and the mixture was cooled to room temperature to be solidified. The solid was collected by filtration to yield the titled compound (108.92 mg).

Figure 9:
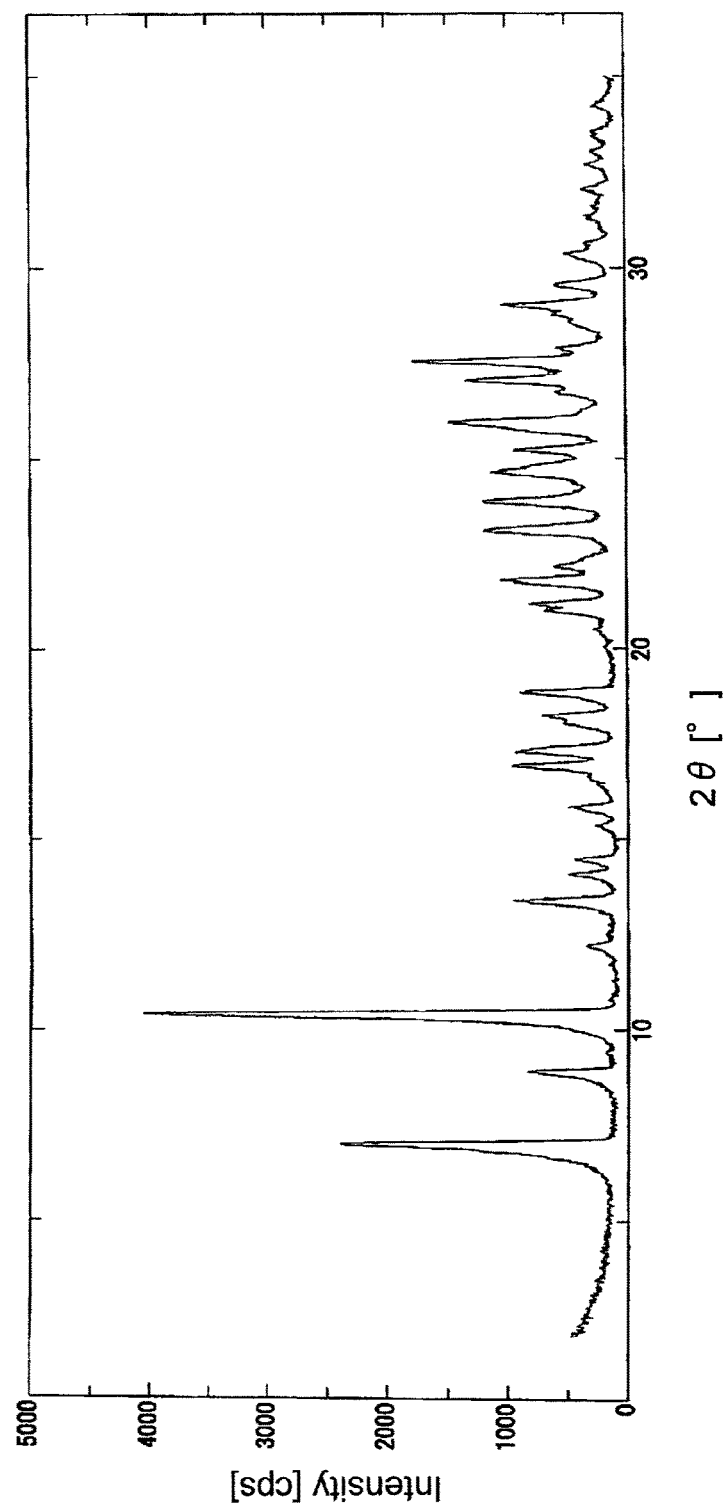
FIG. 9 shows an X-ray powder diffraction pattern for the hydrobromide obtained in Example 10.

X-ray diffraction data (diffraction angle (2θ)/relative intensity): 7.00°/61, 8.92°/21, 10.44°/100, 13.38°/24, 16.94°/25, 17.30°/23, 18.86°/21, 21.18°/21, 21.82°/25, 23.10°/30 and 25.98°/37. Of these peaks, particularly characteristic peaks were at 7.00°, 8.92° and 10.44°. FIG. 9 shows an X-ray diffraction pattern.

EXAMPLE 11

Methyl N-[3-(6,7-dimethoxy-2-methylamino-quinazolin-4-yl)phenyl]terephthalamic acid sulfate Dimethyl sulfoxide (1 mL) and sulfuric acid (26 μL) were added to and dissolved in methyl N-[3-(6,7-dimethoxy-2-methylaminoquinazolin-4-yl)phenyl]terephthalamic acid (103.92 mg) by heating. Then, 2-propanol (3 mL) was added to the mixture and the mixture was cooled to room temperature to be solidified. The solid was collected by filtration to yield the titled compound (112.12 mg).

Figure 10:
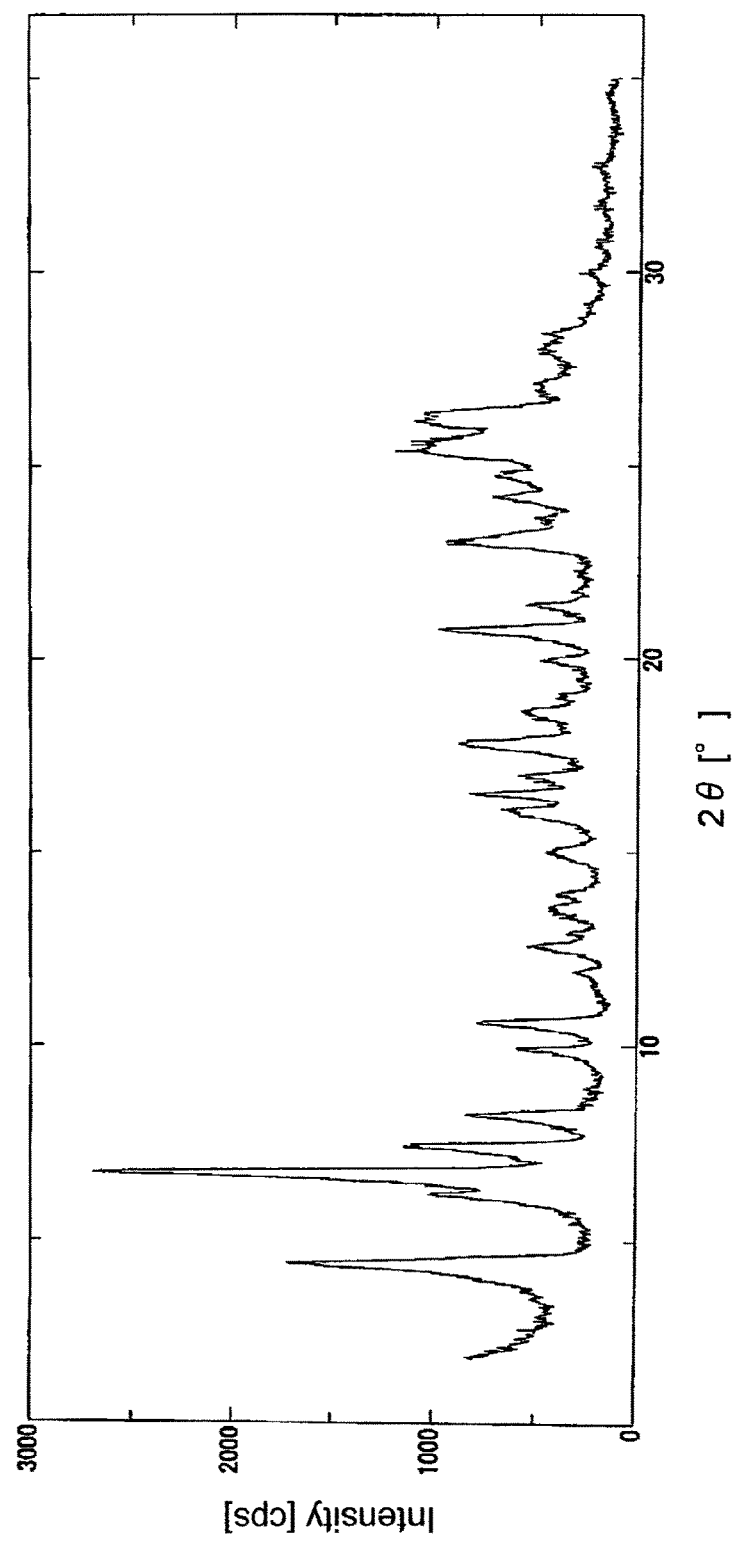
FIG. 10 shows an X-ray powder diffraction pattern for the sulfate obtained in Example 11.

X-ray diffraction data (diffraction angle (2θ)/relative intensity): 4.42°/68, 6.76°/100, 7.46°/44, 8.22°/34, 17.88°/33 and 22.98°/38. Of these peaks, particularly characteristic peaks were at 4.42°, 6.76° and 7.46°. FIG. 10 shows an X-ray diffraction pattern.

EXAMPLE 12

Methyl N-[3-(6,7-dimethoxy-2-methylamino-quinazolin-4-yl)phenyl]terephthalamic acid methanesulfonate Dimethyl sulfoxide (1 mL) and methanesulfonic acid (22 μL) were added to methyl N-[3-(6,7-dimethoxy-2-methylaminoquinazolin-4-yl)phenyl]terephthalamic acid (98.58 mg). Dimethyl sulfoxide (1.5 mL) was added to and dissolved in the mixture while heating the mixture, and then 2-propanol (15 mL) was added to the mixture and the mixture was cooled to room temperature to be solidified. The solid was collected by filtration to yield the titled compound (119.47 mg).

Figure 11:
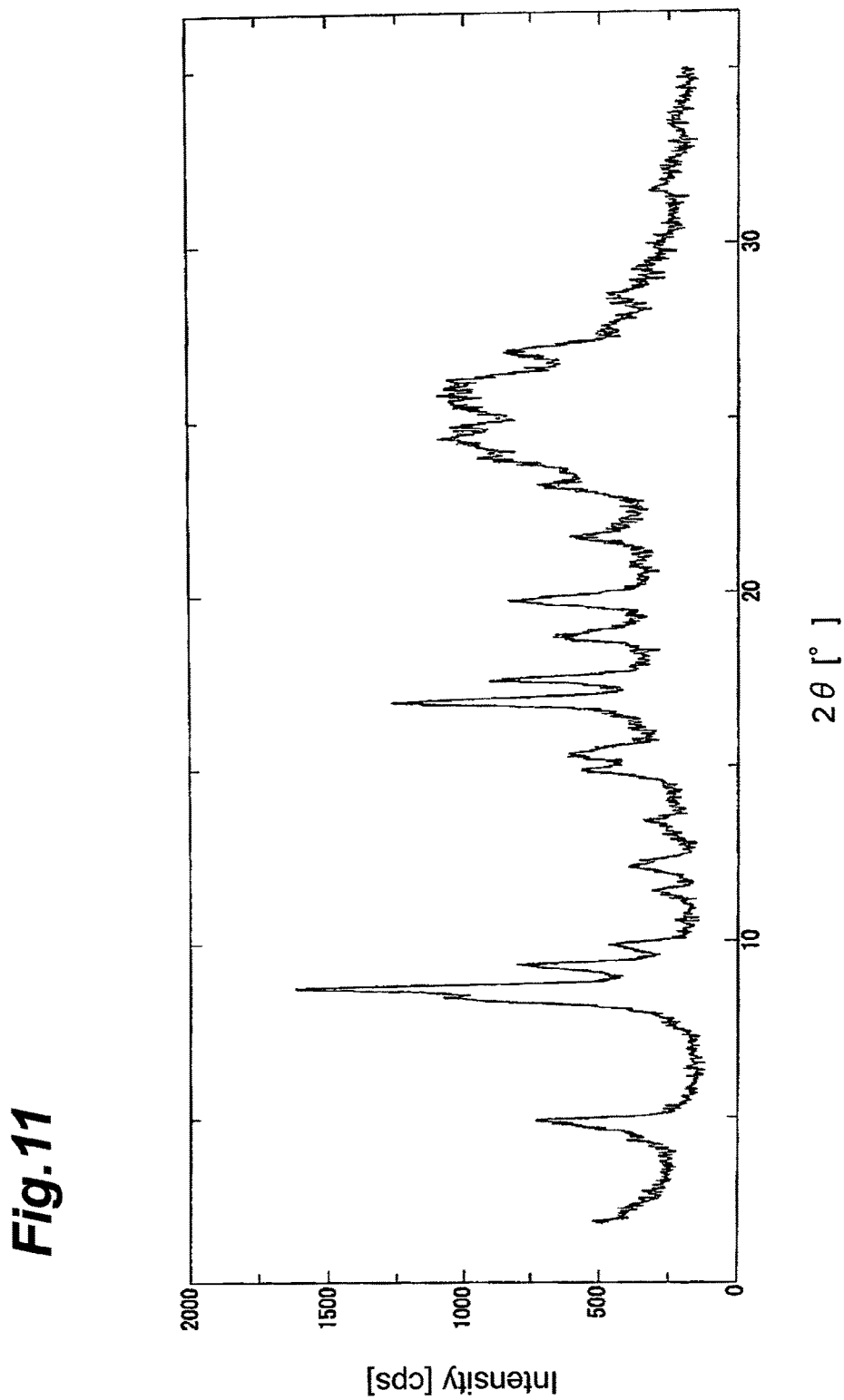
FIG. 11 shows an X-ray powder diffraction pattern for the methanesulfonate obtained in Example 12.

X-ray diffraction data (diffraction angle (2θ)/relative intensity): 4.92°/46, 8.72°/100, 9.36°/50, 16.90°/79, 17.56°/54 and 19.78°/52. Of these peaks, particularly characteristic peaks were at 4.92°, 8.72° and 19.78°. FIG. 11 shows an X-ray diffraction pattern.

EXAMPLE 13

Methyl N-[3-(6,7-dimethoxy-2-methylamino-quinazolin-4-yl)phenyl]terephthalamic acid p-toluenesulfonate Dimethyl sulfoxide (1 mL) and p-toluenesulfonic acid monohydrate (47.98 mg) were added to methyl N-[3-(6,7-dimethoxy-2-methylaminoquinazolin-4-yl)phenyl]terephthalamic acid (106.56 mg). The mixture was heated to be dissolved, and then 2-propanol (5 mL) was added to the mixture and the mixture was cooled to room temperature to be solidified. The solid was collected by filtration to yield the titled compound (57.34 mg).

Figure 12:
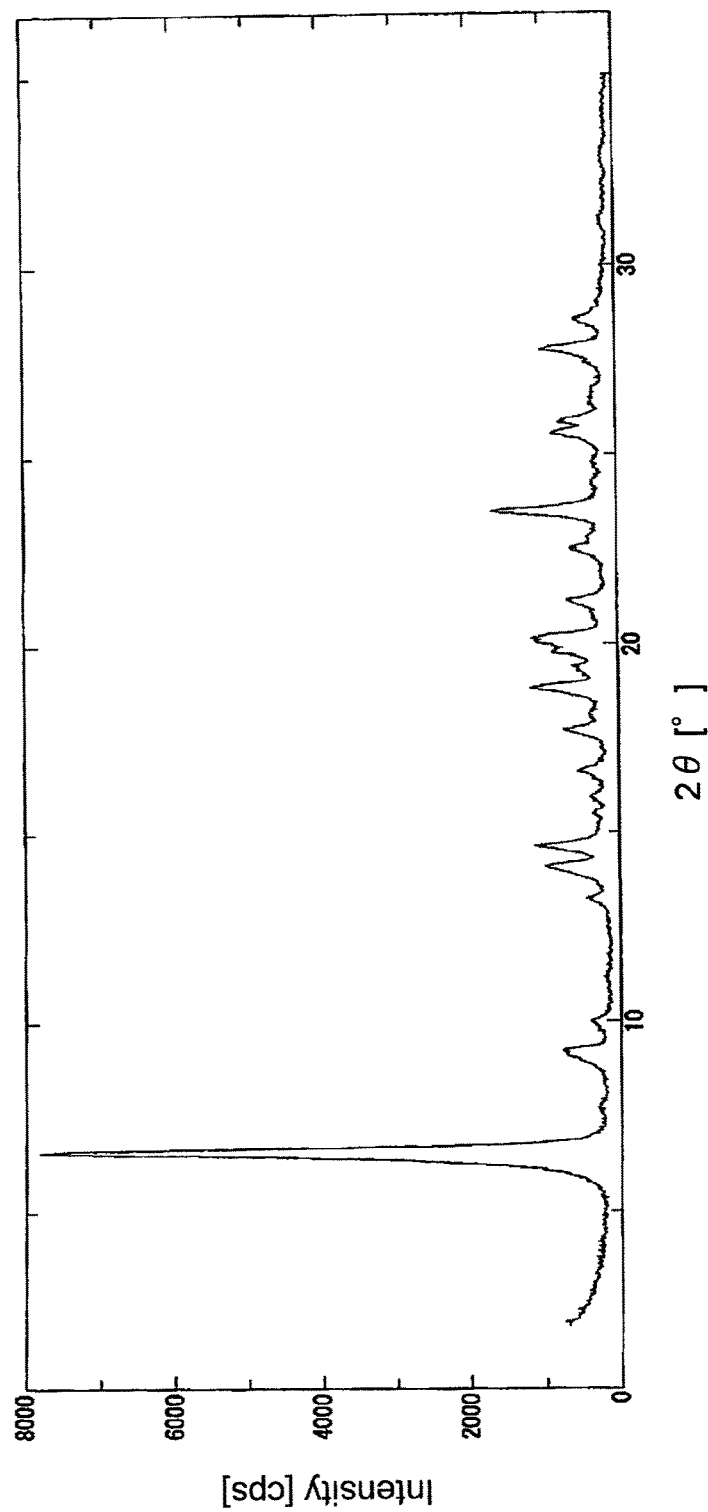
FIG. 12 shows an X-ray powder diffraction pattern for the p-toluenesulfonate obtained in Example 13.

X-ray diffraction data (diffraction angle (2θ)/relative intensity): 6.60°/100, 9.240/10, 14.12°/13, 14.64°/15, 20.06°/14 and 23.56°/21. Of these peaks, particularly characteristic peaks were at 6.60°, 9.24° and 14.12°. FIG. 12 shows an X-ray diffraction pattern.

EXAMPLE 14

Methyl N-[3-(6,7-dimethoxy-2-methylamino-quinazolin-4-yl)phenyl]terephthalamic acid phosphate Dimethyl sulfoxide (1 mL) and phosphoric acid (25 μL) were added to methyl N-[3-(6,7-dimethoxy-2-methylaminoquinazolin-4-yl)phenyl]terephthalamic acid (96.52 mg). Dimethyl sulfoxide (0.75 mL) was added to and dissolved in the mixture while heating the mixture, and then 2-propanol (2 mL) was added to the mixture and the mixture was cooled to room temperature to be solidified. The solid was collected by filtration to yield the titled compound (114.15 mg).

Figure 13:
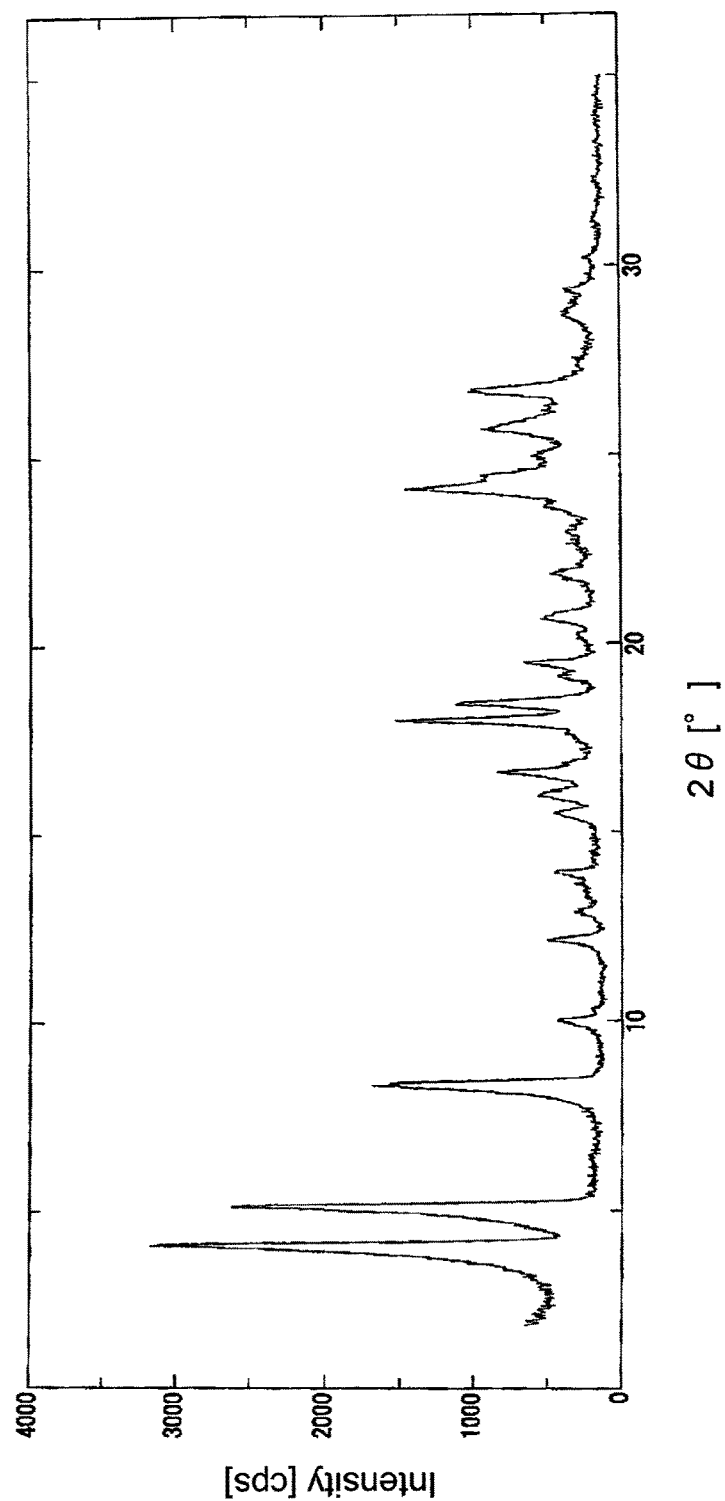
FIG. 13 shows an X-ray powder diffraction pattern for the phosphate obtained in Example 14.

X-ray diffraction data (diffraction angle (2θ)/relative intensity): 4.10°/100, 5.12°/83, 8.38°/51, 12.16°/17, 17.98°/50 and 18.44°/35. Of these peaks, particularly characteristic peaks were at 4.10°, 5.12° and 8.38°. FIG. 13 shows an X-ray diffraction pattern.

Measurement of $^{13}$C Solid NMR spectrum

Figure 16:
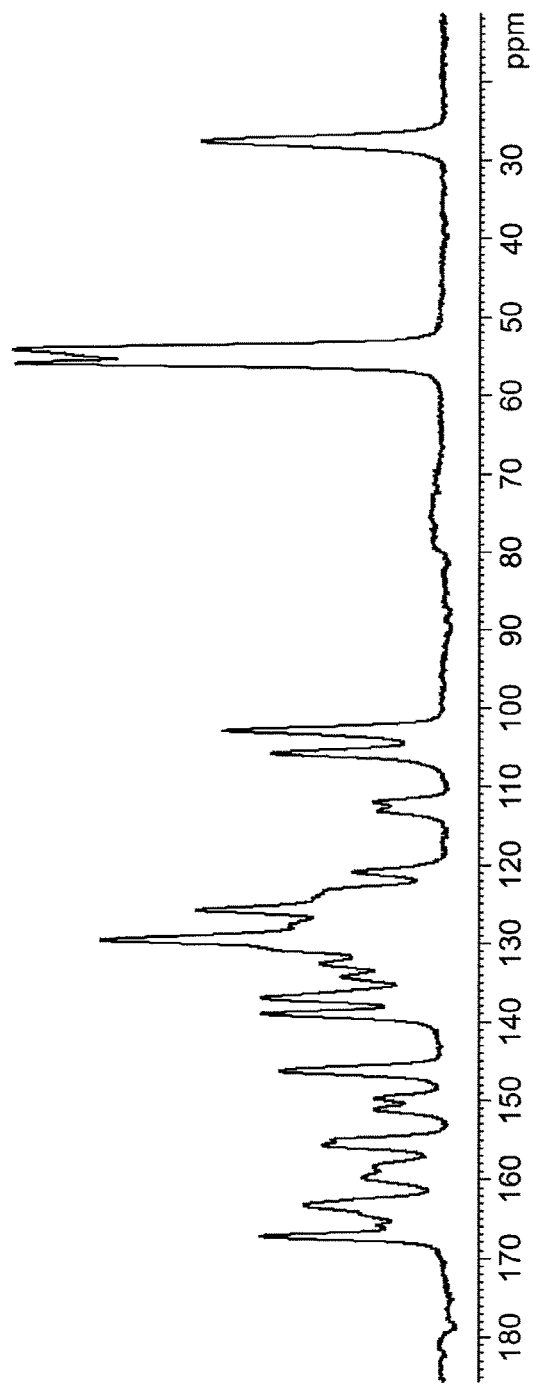
FIG. 16 shows a $^{13}C$ solid NMR spectrum for the crystals obtained in Example 2.

A $^{13}$C solid NMR spectrum of the crystals obtained in Example 2 was carried out under the following conditions. The spectrum is shown in FIG. 16 and the chemical shifts are summarized in Table 1. Characteristic peaks are observed at 146.19 ppm, 102.78 ppm and 27.47 ppm.

Measuring apparatus: AVANCE 400 (Bruker)
Probe: 7 mm-CP/MAS (Bruker)
Cell spinning rate: 5000 Hz
Measuring method: CP/TOSS method
Contact time: 1000 milliseconds
Latency time: 3 seconds
Repeat count: 5120
External standard: The chemical shift for the carbonyl carbon of glycine was set as 176.03 ppm.

TABLE 1

| | |
|---|---|
| 167.10 | 132.52 |
| 165.70 | 129.38 |
| 163.16 | 125.65 |
| 159.69 | 120.86 |
| 158.37 | 113.11 |
| 155.56 | 111.94 |
| 151.09 | 105.71 |
| 149.68 | 102.78 |
| 146.19 | 55.70 |
| 138.88 | 53.96 |
| 136.86 | 27.47 |
| 134.21 | | ppm

In order to confirm the effect of the compound of Example 1 as an antipruritic agent, the present inventors have conducted the following test.

TEST EXAMPLE 1

Evaluation of Compounds in Oxazolone-Induced Scratching Behavior Model

<Test Method>

As test animals, commercially available 5-week-old NC/Nga female mice (Japan SLC, Inc. and CRJ, Inc.) were used. For acclimation, the mice passed a preliminary breeding period of 7 days. Thereafter, only animals, wherein no changes were found in a general state and the body weight was favorably increased, were used for the test.

(1) Sensitization and Induction

Sensitization was carried out by applying once 20 μL of an acetone solution (Wako Pure Chemical Industries, Ltd.) that contained 0.5% 4-ethoxymethylene-2-phenyl-2-oxazolin-5-one (hereinafter abbreviated as "oxazolone"; Sigma) to each of the left and right pinnas of 6-week-old mice, which had passed an acclimation period.

Induction was carried out by applying 10 μL of 0.3% oxazolone to the left pinna of each mouse, 3 times in total, at intervals of 2 or 3 days from the 5th day after sensitization.

(2) Measurement of Scratching Behavior

For objective evaluation, the scratching behavior of each mouse was automatically measured using a Micro Act device (NeuroScience, Inc.). A magnet piece (diameter: 1 mm; length: 3 mm; NeuroScience) was inserted into the skin of the left hind-leg of each mouse anesthetized with diethyl ether (Wako Pure Chemical Industries, Ltd.) by the day before the measurement at the latest. Immediately after scratching behavior had been induced by application of oxazolone, the mouse was transferred into a chamber (diameter: 11 cm; height: 18 cm) with a coil. Thereafter, electric current induced by the movement of the magnet inserted into the leg of the mouse was measured for a certain period of time. A characteristic wave form that reflects such scratching behavior was detected by the Micro Act device, and the appearance frequency of the detected wave form was counted as a number of scratching behaviors.

(3) Evaluation of Test Substance

Preparation of test substance: The compound of Example 1 was prepared at a concentration of 0.3% in a mixed solvent (acetone:ethanol=1:1).

With regard to the groups of test substances, the following 3 groups were determined: (1) normal group—a mixed solvent (acetone:ethanol=1:1) application group; (2) control group—a mixed solvent (acetone:ethanol=1:1) application group; (3) a compound of Example 1 application group. The mice were divided into each group, such that the number of scratching behaviors became uniform based on the number of scratching behaviors obtained during the 2nd induction.

Evaluation of test substance: Ten microliters of a test substance (only the mixed solvent (acetone:ethanol=1:1) was applied to the normal group and the control group) was administered 1 hour before the 3rd application of oxazolone. Evaluation of the test substance was carried out, using, as an indicator, the number of scratching behaviors obtained during 2 hours after induction due to the 3rd application of oxazolone (the mixed solvent (acetone:ethanol=1:1) was applied to the normal group). In addition, another evaluation was carried out based on cutaneous symptom. That is to say, with regard to findings of scratching behaviors obtained at 1 day before the 3rd application of oxazolone and at 1 day or 4 days after the application, namely, with regard to each of the items of (1) abrasion and (2) bleeding/erosion, 4 stages of rating ranging from 0 to 3 (0: no symptoms; 1: slight; 2: moderate; and 3: serious) was carried out. Thus, using the difference in scores obtained before and after induction with oxazolone as an indicator, the scratching behavior was evaluated. Such rating was carried out for every item, and the total score was defined as the score of each individual.

<Test Results>

Figure 14:
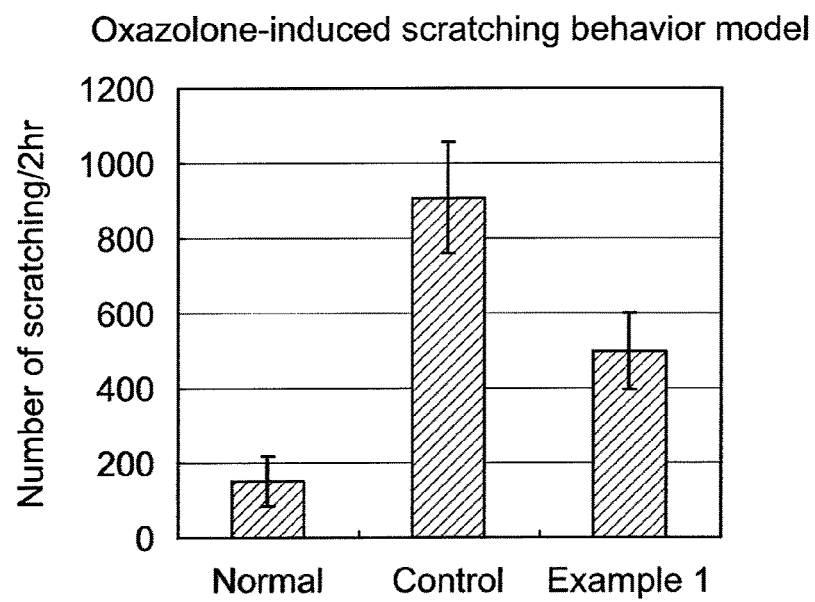
FIG. 14 shows the number of scratching behaviors of oxazolone-induced mice.

(1) The measurement results regarding the number of scratching behaviors are shown in FIG. 14 (normal group: n=11; the other groups: n=17 in FIG. 14).

Figure 15:
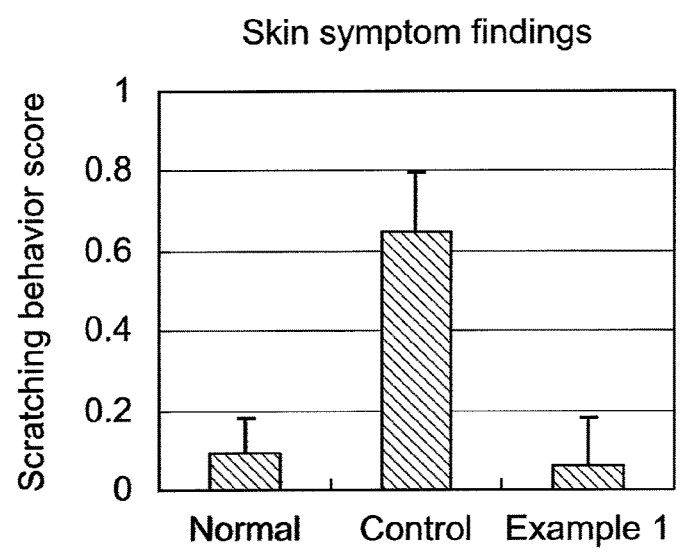
FIG. 15 shows the result of skin symptom findings (after one day) of oxazolone-induced mice.

(2) The measurement results regarding cutaneous symptoms are shown in FIG. 15. FIG. 15 is a graph made based on the value obtained by subtracting the score obtained before administration from the score obtained 1 day after administration (normal group: n=11; the other groups: n=17 in FIG. 15).

From these results, it was found that the compound of Example 1 suppress scratching behavior and also suppresses deterioration in cutaneous symptoms caused by such scratching behavior, thereby having an excellent antipruritic effect.

TEST EXAMPLE 2

Experiment to Evaluate Induction Potency of Drug Metabolizing Enzyme (CYP) Using Cryopreserved Human Hepatocytes <Test Operations>

Cryopreserved human hepatocytes (XenoTeck) were rapidly thawed at 37° C., and viable cells were obtained using Hepatocytes Isolation Kit (Nosan Corporation). After cells prepared were diluted with ice cold William's Medium E (10% FBS, +PSG) to give a concentration of $5\times10^5$ viable cells/mL, the cells were seeded onto a 48-well collagen-coated plate (BD Biosciences) at a concentration of $1\times10^5$ cells/cm² and cultured at 37° C. in 5% $CO_2$ for 24 hours. Then, the medium was replaced with Hepato-STIM (registered trade mark: BD Biosciences) (+EGF, PSG, −FBS), and the cells were further cultured at 37° C. in 5% $CO_2$ for 24 hours. Hepato-STIM(+EGF, PSG, −FBS) was used as culture medium, and the cells were incubated with culture medium containing test compound, β-naphthoflavone (hereinafter abbreviated as β-NF, SIGMA) used as a positive control of human CYP1A, or rifampicin (hereinafter abbreviated as Rif, Wako Pure Chemical Industries, Ltd.) used as a positive control of human CYP3A4 at 37° C. in 5% $CO_2$ for approximately 48 hours. The culture medium containing test compound, β-NF or Rif was replaced every 24 hours. Test compound, β-NF and Rif were each dissolved in dimethyl sulfoxide (DMSO: Wako Pure Chemical Industries, Ltd.), and culture medium containing test compound (final concentrations; 1, 3 and 10 μM), β-NF (final concentration; 10 μM) or Rif (final concentration; 10 μM) was prepared by adding them to Hepato-STIM(+EGF, PSG, −FBS), respectively. Final concentration of DMSO was set to be 0.1%, and culture medium containing 0.1% DMSO was used for control. After completion of the treatment, the cells were washed with PBS once, and total RNA was purified using Total RNA Purification Kit (Applied Biosystems). The purified total RNA was subjected to reverse transcription reaction using TaqMan Reverse Transcription Reagents (Applied Biosystems) to synthesize cDNA, where oligo dT was used as a primer. The reaction was carried out using GeneAmp PCR system 9700 at 25° C. for 10 minutes, followed by at 48° C. for 60 minutes. Then, reverse transcriptase was deactivated at 95° C. for 10 minutes. The levels of mRNA for CYP1A1 and GAPDH were quantified using SYBR Green PCR Core Reagents Kit (Applied Biosystems), and those for CYP1A2 and that of CYP3A4 were measured using Taqman PCR Core Reagents Kit (Applied Biosystems) and ABI Prism 7900 Sequence Detection System (Applied Biosystems). Primer sequences and PCR conditions used for quantification of each mRNA are shown in Tables 2 and 3, respectively.

PCR Conditions

TABLE 3

| Temperature | Time | |
|---|---|---|
| 95 | 10 min | |
| 94 | 15 sec | Denaturation |
| 58 | 20 sec | Annealing |
| 72 | 30 sec | Elongation reaction |

* A cycle consisting of denaturation, annealing, and elongation reaction, was repeated 50 times.

<Calculation of Ability to Induce CYP>

The ability of a test compound to induce CYP1A1 was calculated as follows:

Ability of a test compound to induce CYP1A1 (%)=
{[(amount of mRNA of CYP1A1 in test compound treated cells)/(amount of mRNA of GAPDH in test compound treated cells)]/
[(amount of mRNA of CYP1A1 in control cells)/(amount of mRNA of GAPDH in control cells)]−1}/{[(amount of mRNA of CYP1A1 in positive control treated cells)/(amount of mRNA of GAPDH in positive control treated cells)]/
[(amount of mRNA of CYP1A1 in control cells)/(amount of mRNA of GAPDH in control cells)]−1}×100

The ability to induce CYP1A2 or CYP3A4 was calculated in the same manner described above.

<Test Results>

The results regarding the compound of Example 1 are shown in Table 4. As a comparative example, the compound described as Example 1 in WO99/37622 (4-(3-benzoylaminophenyl)-6,7-dimethoxy-2-methylaminoquinalozine) was used.

The results indicated that the compound of Example 1 shows lower induction potency on CYPs than the compound of the comparative example.

TABLE 4

| | Induction Ability compared to positive control (%) | | | |
|---|---|---|---|---|
| | | CYP1A1 | CYP1A2 | CYP3A4 |
| Rifampicin | 10 μM | | | 100.0 |
| β-naphthoflavone | 10 μM | 100.0 | 100.0 | |
| | 1 μM | 0.1 | −0.1 | −2.4 |
| Example 1 | 3 μM | 0.6 | −0.7 | −3.4 |
| | 10 μM | 4.6 | 2.5 | −4.0 |
| | 1 μM | 2.1 | 7.2 | 1.6 |

Primer Sequences

TABLE 2

| Target | Name | Sequence | |
|---|---|---|---|
| CYP1A1 | hCYP1A1_F1 | tggtctcccttctctacactcttgt | (SEQ ID NO: 1) |
| | hCYP1A1_R1 | attttccctattacattaaatcaatggttct | (SEQ ID NO: 2) |
| CYP1A2 | hCYP1A2_F_EJCP | gttcctgcagaaaacagtcca | (SEQ ID NO: 3) |
| | hCYP1A2_R_EJCP | ctgtgcttgaacagggcac | (SEQ ID NO: 4) |
| | hCYP1A2_probe_EJCP | agcactatcaggactttgacaagaacagtgtct | (SEQ ID NO: 5) |
| CYP3A4 | hCYP3A4_F_m | gcaggaggaaattgatgcagtt | (SEQ ID NO: 6) |
| | hCYP3A4_R_x | gtcaagatactccatctgtagcacagt | (SEQ ID NO: 7) |
| | hCYP3A4_probe_m | Acccaataaggcaccacccacctatga | (SEQ ID NO: 8) |
| GAPDH | hGAPDH_F | gaaggtgaaggtcggagtc | (SEQ ID NO: 9) |
| | hGAPDH_R | gaagatggtgatgggatttc | (SEQ ID NO: 10) |

TABLE 4-continued

| | Induction Ability compared to positive control (%) | | |
| --- | --- | --- | --- |
| | CYP1A1 | CYP1A2 | CYP3A4 |
| Comparative example   3 μM | 18.5 | 34.3 | 10.8 |
| 10 μM | 51.9 | 35.0 | 17.0 |

INDUSTRIAL APPLICABILITY

The present invention can provide crystals, amorphous substances, salts and salt hydrates of a compound which can be an agent useful for itch caused by atopic disease or the like. rmatitis.

What is claimed is:

1. Crystals of methyl N-[3-(6,7-dimethoxy-2-methylaminoquinazolin-4-yl)phenyl]terephthalamic acid, which have diffraction peaks at diffraction angles (2θ±0.2°) of 8.2°, 16.5° and 24.5° in an X-ray powder diffraction or peaks at chemical shifts of approximately 146.19 ppm, approximately 102.78 ppm and approximately 27.47 ppm in a $^{13}$C solid NMR spectrum.

* * * * *

SEQUENCE LISTING

<160> NUMBER OF SEQ ID NOS: 10

<210> SEQ ID NO 1
<211> LENGTH: 25
<212> TYPE: DNA
<213> ORGANISM: Artificial Sequence
<220> FEATURE:
<223> OTHER INFORMATION: Synthetic forward primer for CYP1A1: hCYP1A1_F1

<400> SEQUENCE: 1
tggtctccct tctctacact cttgt                                        25

<210> SEQ ID NO 2
<211> LENGTH: 31
<212> TYPE: DNA
<213> ORGANISM: Artificial Sequence
<220> FEATURE:
<223> OTHER INFORMATION: Synthetic reverse primer for CYP1A1: hCYP1A1_R1

<400> SEQUENCE: 2
attttcccta ttacattaaa tcaatggttc t                                 31

<210> SEQ ID NO 3
<211> LENGTH: 21
<212> TYPE: DNA
<213> ORGANISM: Artificial Sequence
<220> FEATURE:
<223> OTHER INFORMATION: Synthetic forward primer for CYP1A2:
      hCYP1A2_F_EJCP

<400> SEQUENCE: 3
gttcctgcag aaaacagtcc a                                            21

<210> SEQ ID NO 4
<211> LENGTH: 19
<212> TYPE: DNA
<213> ORGANISM: Artificial Sequence
<220> FEATURE:
<223> OTHER INFORMATION: Synthetic reverse primer for CYP1A2:
      hCYP1A2_R_EJCP

<400> SEQUENCE: 4
ctgtgcttga acagggcac                                               19

<210> SEQ ID NO 5
<211> LENGTH: 33
<212> TYPE: DNA
<213> ORGANISM: Artificial Sequence
<220> FEATURE:
<223> OTHER INFORMATION: Synthetic probe for CYP1A2: hCYP1A2_probe_EJCP

<400> SEQUENCE: 5
agcactatca ggactttgac aagaacagtg tct                               33

<210> SEQ ID NO 6

-continued

```
<211> LENGTH: 22
<212> TYPE: DNA
<213> ORGANISM: Artificial Sequence
<220> FEATURE:
<223> OTHER INFORMATION: Synthetic forward primer for CYP3A4:
      hCYP3A4_F_m

<400> SEQUENCE: 6
gcaggaggaa attgatgcag tt                                               22

<210> SEQ ID NO 7
<211> LENGTH: 27
<212> TYPE: DNA
<213> ORGANISM: Artificial Sequence
<220> FEATURE:
<223> OTHER INFORMATION: Synthetic reverse primer for CYP3A4:
      hCYP3A4_R_x

<400> SEQUENCE: 7
gtcaagatac tccatctgta gcacagt                                          27

<210> SEQ ID NO 8
<211> LENGTH: 27
<212> TYPE: DNA
<213> ORGANISM: Artificial Sequence
<220> FEATURE:
<223> OTHER INFORMATION: Synthetic probe for CYP3A4: hCYP3A4_probe_m

<400> SEQUENCE: 8
acccaataag gcaccaccca cctatga                                          27

<210> SEQ ID NO 9
<211> LENGTH: 19
<212> TYPE: DNA
<213> ORGANISM: Artificial Sequence
<220> FEATURE:
<223> OTHER INFORMATION: Synthetic forward primer for GAPDH: hGAPDH_F

<400> SEQUENCE: 9
gaaggtgaag gtcggagtc                                                   19

<210> SEQ ID NO 10
<211> LENGTH: 20
<212> TYPE: DNA
<213> ORGANISM: Artificial Sequence
<220> FEATURE:
<223> OTHER INFORMATION: Synthetic reverse primer for GAPDH: hGAPDH_R

<400> SEQUENCE: 10
gaagatggtg atgggatttc                                                  20
```